(12) United States Patent
Resnati et al.

(10) Patent No.: US 7,951,589 B2
(45) Date of Patent: May 31, 2011

(54) MONOCLONAL ANTIBODIES SPECIFIC FOR THE CHEMOTACTIC EPITOPE OF THE UROKINASE-TYPE PLASMINOGEN ACTIVATOR RECEPTOR

(75) Inventors: Massimo Resnati, Macherio (IT); Francesco Blasi, Segrate (IT); Nicolai Sidenius, Pieve Emanuele (IT); Isabella Pallavicini, Briosco (IT)

(73) Assignee: Wilex AG, Munich (DE)

( * ) Notice: Subject to any disclaimer, the term of this patent is extended or adjusted under 35 U.S.C. 154(b) by 893 days.

(21) Appl. No.: 11/814,093

(22) PCT Filed: Mar. 10, 2006

(86) PCT No.: PCT/EP2006/002243
§ 371 (c)(1),
(2), (4) Date: Jul. 17, 2007

(87) PCT Pub. No.: WO2006/094828
PCT Pub. Date: Sep. 14, 2006

(65) Prior Publication Data
US 2009/0202550 A1    Aug. 13, 2009

(30) Foreign Application Priority Data
Mar. 11, 2005 (EP) .................................. 05005374

(51) Int. Cl.
*C07K 14/705* (2006.01)
*C07K 16/28* (2006.01)
*C12N 5/00* (2006.01)
*C12P 21/08* (2006.01)

(52) U.S. Cl. ........ 435/326; 435/331; 435/334; 530/350; 530/387.1; 530/387.3; 530/388.1; 530/388.22; 530/391.3

(58) Field of Classification Search ....................... None
See application file for complete search history.

(56) References Cited

FOREIGN PATENT DOCUMENTS
WO    WO 02/058714 A    8/2002

OTHER PUBLICATIONS

Colcher et al. Effects of genetic engineering on the pharmacokinetics of antibodies. Q J Nucl Med 43(2): 132-139, 1999.*
Sidenius et al. Shedding and cleavage of the urokinase receptor (uPAR): identification and characterisation of uPAR fragments in vitro and in vivo. FEBS Letter 475: 52-56, 2000.*
Carriero et al. Tissue distribution of soluble and receptor-bound urokinase in human breast cancer using a panel of monoclonal antibodies. Cancer Res 54: 5445-5454, 1994.*
Furlan et al. The soluble D2D3(88-274) fragment of the urokinase receptor inhibits monocyte chemotaxis and integrin. independent cell adhesion. J Cell Sci 117: 2909-2916, 2004.*
Resnati et al. Specific immunofluorimetric assay detecting the chemotactic epitope of the urokinase receptor (uPAR). J Immunol Methods 308: 192-202, 2006.*
Albrecht et al. "CD87 Workshop: Epitope-mapped monoclonal antibodies directed to the human urokinase receptor (uPAR, CD87)". Leucocyte Typing VI: White cell differentiation antigens: proceedings of the 6th international workshop and conference held in Kobe, Japan, Nov. 10-14, 1996. Garland Pub: New York, 1997, pp. 1023-1025.*

* cited by examiner

*Primary Examiner* — Bridget E Bunner
(74) *Attorney, Agent, or Firm* — Rothwell, Figg, Ernst & Manbeck, P.C.

(57) ABSTRACT

The present invention describes monoclonal antibodies specific for the chemotactic epitope of the uPAR. In particular, the invention comprises monoclonal antibodies against uPAR fragments specifically recognizing in whole or in part the chemotactic sequence of uPAR connecting domain 1 to domain 2.

35 Claims, 20 Drawing Sheets

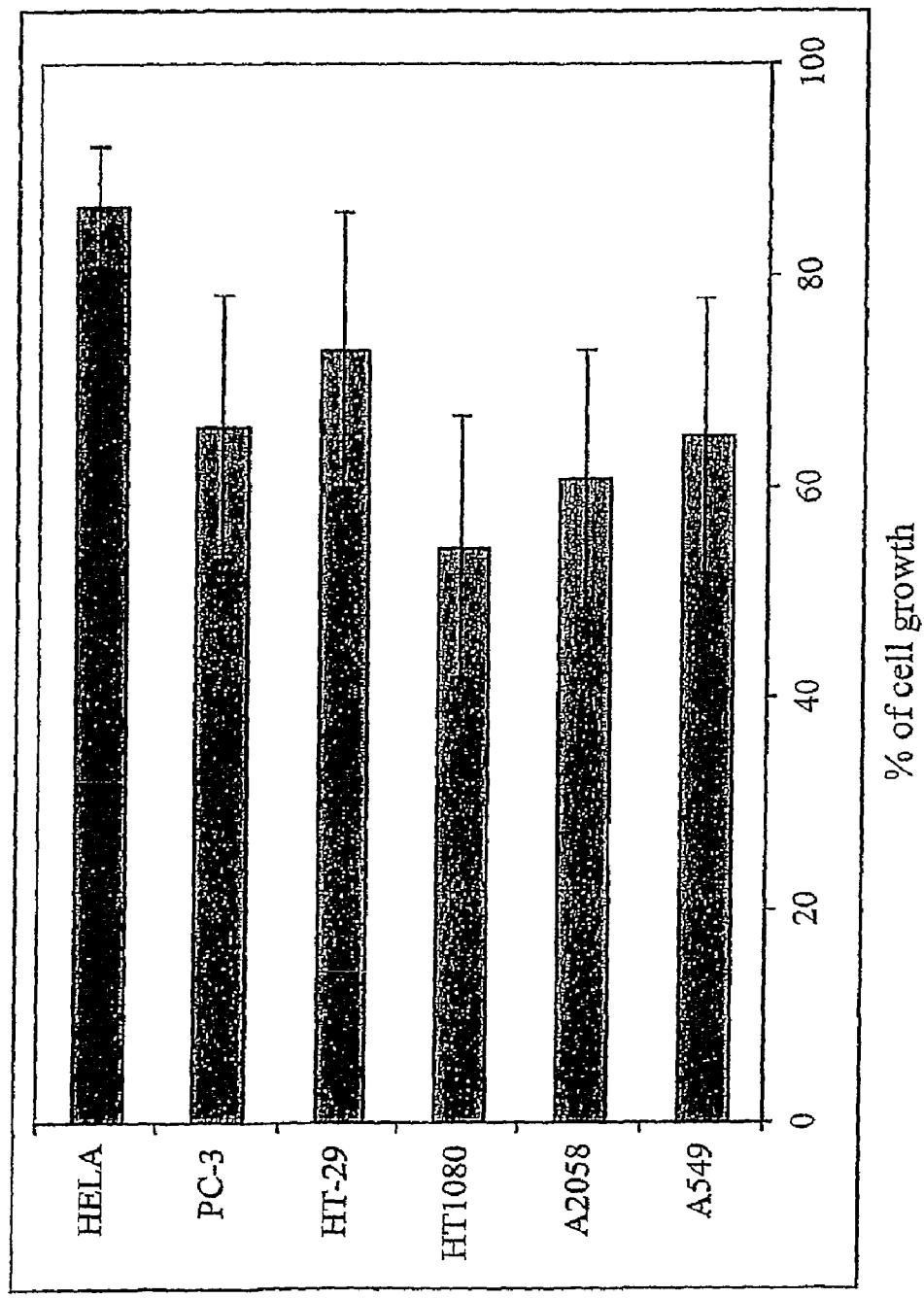
Figure 12A: Effect of Mab 8D3 in tumor cell growth.

Heavy chain

SEQ ID NO:1
Nucleotide sequence of the variable region (CDR sequences are underlined)

AGGTGCAGCT GCAGGAGTCA GGACCTGAGC TGAAGAAGCC TGGAGAGACA
GTCAAGATCT CCTGCAAGGC TTCTGGTTAT ACCTTCACAG ACTATTCAAT
GCACTGGGTG AAGCAGGCTC CAGGAAAGGG TTTAAAGTGT ATGGGCTGGA
TAAACACTGA GACCACTAAG TCAACATATG CAGATGACTT CAAGGGACGG
TTTGCCCTCT CTTTGGAAAC CTCTGCCAGC ACTGTCTATT TGCAGATCAG
CAACCTCAAA AATGAGGACA CGGCTACATA TTTCTGTGCT AGAGAGGCCT
CATATGGTGA GTTTGACTAC TGGGGCCAAG GGACCACGGT CACCGTCTCC
TCA

SEQ ID NO:2
Amino acid sequence of the variable region, deduced from the nucleotide sequence and confirmed by peptide mass fingerprint (underlined)

VQLQESGPEL KKPGETVKIS CKASGYTFTD YSMHWVKQAP GKGLKCMGWI
NTETTKSTYA DDFKGRFALS LETSASTVYL QISNLKNEDT ATYFCAREAS
YGEFDYWGQG TTVTVSS

Light chain

SEQ ID NO:3
Nucleotide sequence of the variable region (CDR sequences are underlined)

GACATTGTGC TAACCCAGTC TCCAGCTTCC TTAGCTGTAT CTCTGGGGCA
GAGGGCCACC ATCTCATGCA GGGCCAGCAA AAGTGTCAGT ACATCTGGCT
ATAGTTATAT GCACTGGTAC CAACAGAAAC CAGGACAGCC ACCCAAACTC
CTCATCTATC TTGCATCCAA CCTCGAATCT GGGGTCCCTG CCAGGTTCAG
TGGCAGTGGG TCTGGGACAG ACTTCACCCT CGACATCCAT CCTGTAGAGG
AGGAGGATGC TGCAACCTAT TACTGTCAGC ACAGTAGGGA GCTTCCGTAC
ACGTTCGGAG GGGGACCAA GCTGGAGCTG AAACGG

SEQ ID NO:4
Amino acid sequence of the variable region, deduced from the nucleotide sequence and confirmed by peptide mass fingerprint (underlined)

DIVLTQSPAS LAVSLGQRAT ISCRASKSVS TSGYSYMHWY QQKPGQPPKL
LIYLASNLES GVPARFSGSG SGTDFTLDIH PVEEEDAATY YCQHSRELPY
TFGGGTKLEL KR

8D3

Heavy chain

SEQ ID NO:5
Nucleotide sequence of the variable region (CDR sequences are underlined)

CAGATCCAGT TGGTGCAGTC TGGACCTGAG CTGAAGAAGC CTGGAGAGAC
AGTCAAGATC TCCTGCAAGG CTTCTGGTTA TACCTTCACA <u>GACTATTCAA
TGCACTGGAT</u> GAAGCAGGCT CCAGGAAGGG ATTTAAAGTG GATGGGCTGG
<u>ATAAACACTG AGACTGGTGA GACAAAATAT</u> GCAGCTGACT TCAGGGACG
GTTTGCCTTC TCTTTGGAAA CCTCTGCCAG CACTGCCTAT TTGCAGATCA
ACAACCTCAA AAATGAGGAC ACGGCTACAT ATTTCTGTTC TAGA<u>GAAACT
GGGACAGGGG CTATGGACTA C</u>TGGGGCCAA GGGACCACGG TCACCGTCTC
CTCA

SEQ ID NO:6
Amino acid sequence of the variable region, deduced from the nucleotide sequence and confirmed by peptide mass fingerprint (underlined)

<u>QIQLVQSGPE LKKPGETVKI SCKASGYTFT</u> DYSMHWMKQA PGRDLKWMGW
<u>INTETGETKY AADFRGRFAF SLETSASTAY LQINNLKNED TATYFCSRET</u>
GTGAMDYWGQ GTTVTVSS

Light chain

SEQ ID NO:7
Nucleotide sequence of the variable region (CDR sequences are underlined)

GAAAATGTGC TCACCCAGTC TCCAGCAATC ATGTCTGCAT CTCTAGGGGA
ACGGGTCACC ATGACCTGCA <u>CTGCCAGCTC AAGTGTAAGT TCCAGTTACT
TGCACTGGTA</u> CCAGCAGAAG CCAGGATCCT CCCCCAAACT CTGGATTTAT
<u>AGCACATCCA ACCTGGCTTC T</u>GGAGTCCCA GCTCGCTTCA GTGGCAGTGG
GTCTGGGACC TCTTACTCTC TCACAATCAG AAGCATGGAG GCTGAAGATG
CTGCCACTTA TTACTGC<u>CAC CAGTATCATC GTTCCCCACC</u> CACGTTCGGA
GGGGGCACCA AGCTGGAAAT CAAACG

SEQ ID NO:8
Amino acid sequence of the variable region, deduced from the nucleotide sequence and confirmed by peptide mass fingerprint (underlined)

ENVLTQSPAI MSASLGE<u>RVT MTCTASSSVS SSYLHWYQQK PGSSPKLWIY
STSNLASGVP ARFSGSGSGT SYSLTIRSME AEDAATYYCH QYHRSPPTFG
GGTKLE</u>IK

Heavy chain

SEQ ID NO:1
Nucleotide sequence of the variable region (CDR sequences are underlined)

AGGTGCAGCT GCAGGAGTCA GGACCTGAGC TGAAGAAGCC TGGAGAGACA
GTCAAGATCT CCTGCAAGGC TTCTGGTTAT ACCTTCACA<u>G</u> <u>ACTATTCAAT</u>
<u>GCAC</u>TGGGTG AAGCAGGCTC CAGGAAAGGG TTTAAAGTGT ATGGGC<u>TGGA</u>
<u>TAAACACTGA GACCACTAAG TCAACATATG CAGATGACTT CAAGGGACGG</u>
TTTGCCCTCT CTTTGGAAAC CTCTGCCAGC ACTGTCTATT TGCAGATCAG
CAACCTCAAA AATGAGGACA CGGCTACATA TTTCTGTGCT AGA<u>GAGGCCT</u>
<u>CATATGGTGA GTTTGACTAC</u> TGGGGCCAAG GGACCACGGT CACCGTCTCC
TCA

SEQ ID NO:2
Amino acid sequence of the variable region, deduced from the nucleotide
sequence and confirmed by peptide mass fingerprint (underlined)

VQLQESGPEL KKPGETVKIS CKA<u>SGYTFTD</u> <u>YSMHWVKQAP</u> GKGLK<u>CMGWI</u>
<u>NTETTKSTYA DDFKGRFALS</u> LETSASTVYL QISNLKNEDT ATYFCAREA<u>S</u>
<u>YGEFDYWGQG</u> TTVTVSS

Light chain

SEQ ID NO:3
Nucleotide sequence of the variable region (CDR sequences are underlined)

GACATTGTGC TAACCCAGTC TCCAGCTTCC TTAGCTGTAT CTCTGGGGCA
GAGGGCCACC ATCTCATGC<u>A</u> <u>GGGCCAGCAA AAGTGTCAGT ACATCTGGCT</u>
<u>ATAGTTATAT GCAC</u>TGGTAC CAACAGAAAC CAGGACAGCC ACCCAAACTC
CTCATCTAT<u>C</u> <u>TTGCATCCAA CCTCGAATCT</u> GGGGTCCCTG CCAGGTTCAG
TGGCAGTGGG TCTGGACAG ACTTCACCCT CGACATCCAT CCTGTAGAGG
AGGAGGATGC TGCAACCTAT TACTGT<u>CAGC ACAGTAGGGA GCTTCCGTAC</u>
<u>ACG</u>TTCGGAG GGGGACCAA GCTGGAGCTG AAACGG

SEQ ID NO:4
Amino acid sequence of the variable region, deduced from the nucleotide
sequence and confirmed by peptide mass fingerprint (underlined)

<u>DIVLTQSPAS LAVSLGQRAT ISCRASKSVS TSGYSYMHWY QQKPGQPPKL
LIYLASNLES GVPARFSGSG SGTDFTLDIH PVEEEDAATY YCQHSRELPY
TFGGGTKLEL</u> KR

Heavy chain

SEQ ID NO:5
Nucleotide sequence of the variable region (CDR sequences are underlined)

CAGATCCAGT TGGTGCAGTC TGGACCTGAG CTGAAGAAGC CTGGAGAGAC
AGTCAAGATC TCCTGCAAGG CTTCTGGTTA TACCTTCACA GACTATTCAA
TGCACTGGAT GAAGCAGGCT CCAGGAAGGG ATTTAAAGTG GATGGGCTGG
ATAAACACTG AGACTGGTGA GACAAAATAT GCAGCTGACT TCAGGGGACG
GTTTGCCTTC TCTTTGGAAA CCTCTGCCAG CACTGCCTAT TTGCAGATCA
ACAACCTCAA AAATGAGGAC ACGGCTACAT ATTTCTGTTC TAGAGAAACT
GGGACAGGGG CTATGGACTA CTGGGGCCAA GGGACCACGG TCACCGTCTC
CTCA

SEQ ID NO:6
Amino acid sequence of the variable region, deduced from the nucleotide
sequence and confirmed by peptide mass fingerprint (underlined)

QIQLVQSGPE LKKPGETVKI SCKASGYTFT DYSMHWMKQA PGRDLKWMGW
INTETGETKY AADFRGRFAF SLETSASTAY LQINNLKNED TATYFCSRET
GTGAMDYWGQ GTTVTVSS

Light chain

SEQ ID NO:7
Nucleotide sequence of the variable region (CDR sequences are underlined)

GAAAATGTGC TCACCCAGTC TCCAGCAATC ATGTCTGCAT CTCTAGGGGA
ACGGGTCACC ATGACCTGCA CTGCCAGCTC AAGTGTAAGT TCCAGTTACT
TGCACTGGTA CCAGCAGAAG CCAGGATCCT CCCCCAAACT CTGGATTTAT
AGCACATCCA ACCTGGCTTC TGGAGTCCCA GCTCGCTTCA GTGGCAGTGG
GTCTGGGACC TCTTACTCTC TCACAATCAG AAGCATGGAG GCTGAAGATG
CTGCCACTTA TTACTGCCAC CAGTATCATC GTTCCCCACC CACGTTCGGA
GGGGGCACCA AGCTGGAAAT CAAACG

SEQ ID NO:8
Amino acid sequence of the variable region, deduced from the nucleotide
sequence and confirmed by peptide mass fingerprint (underlined)

ENVLTQSPAI MSASLGERVT MTCTASSSVS SSYLHWYQQK PGSSPKLWIY
STSNLASGVP ARFSGSGSGT SYSLTIRSME AEDAATYYCH QYHRSPPTFG
GGTKLEIK

US 7,951,589 B2

MONOCLONAL ANTIBODIES SPECIFIC FOR THE CHEMOTACTIC EPITOPE OF THE UROKINASE-TYPE PLASMINOGEN ACTIVATOR RECEPTOR

CROSS REFERENCE TO RELATED APPLICATION

This application is a 35 USC §371 National Phase Entry Application from PCT/EP2006/002243, filed Mar. 10, 2006, and designating the United States.

The present invention describes monoclonal antibodies specific for the chemotactic epitope of the uPAR. In particular, the invention comprises monoclonal antibodies against uPAR fragments specifically recognizing in whole or in part the chemotactic sequence of uPAR connecting domain 1 to domain 2. The present invention also relates to ELISA (Enzyme-Linked Immuno-Sorbent Assay) and immunofluorimetric methods to quantitatively assess the presence of said forms of uPAR, in tissues, extracts and biological fluids. Furthermore, the invention relates to the diagnostic, prognostic and therapeutic use, in particular to the therapy of cancer and/or infectious diseases of the monoclonal antibodies and to a pharmaceutical composition thereof.

Urokinase-type plasminogen activator (uPA) is a serine protease that activates plasminogen to plasmin, a broad-spectrum serine protease. uPA is synthesized as an inactive precursor (pro-uPA) that undergoes proteolytic activation to uPA. Pro-uPA (and uPA) binds with high affinity to a specific plasma membrane receptor, UPAR (CD87) [Vassalli, 1985] [Stoppelli, 1985]. Pro-uPA and uPA are used as thrombolytic agents in both arterial and venous thrombosis. Focusing uPA at the cell surface also is considered an important property exploited by the cancer cells to invade, disseminate and metastasize [Stoppelli, 1986].

uPAR is formed by three repeats, of about 90 residues each, connected by two linker regions defining specific protein domains [Ploug, 2003]. The linker region between domain D1 and D2 is highly susceptible to endoproteolysis caused by proteinases involved in the inflammatory response, such as uPA itself, plasmin, elastase, MMPs and cathepsin G [Koolwijk, 2001] [Hoyer-Hansen, 1992; Hoyer-Hansen, 1997] [Andolfo, 2002] [Beaufort N, 2004]. The amino-terminal domain of UPAR, D1, has been shown to bind uPA directly, although other areas of the receptor (like domain D3) are also relevant in contacting uPA [Behrendt, 1991] [Ploug, 2003]. uPAR is bound to the cell surface via a glycosyl-phosphatidylinositol (GPI) anchor [Ploug, 1991] and hence partially distributes with detergent-resistant membrane microdomains, called "lipid rafts" [Cunningham, 2003].

Binding of uPA to uPAR induces cell migration, cell adhesion and proliferation [Blasi, 2002] [Chapman, 1997] [Preissner, 2000] [Ossowski, 2000]. In addition to extracellular proteolysis, uPAR directly influences cell migration and adhesion, functions that are mediated by integrins in conjunction with seven-trans-membrane receptors [Blasi, 1997]. These activities require the activation of G-proteins, Src-family tyrosine kinases and ERKs [Fazioli, 1997] [Nguyen, 2000] [Degryse, 1999] [Degryse, 2001], [Aguirre Ghiso, 1999] [Resnati, 1996] [Resnati, 2002] [Simon, 2000; Wei, 2001]. The binding of uPA transforms uPAR into a ligand for cell surface trans-membrane proteins (integrins or G protein-coupled Receptors) which can transduce its signal [Ossowski, 2000; Chapman, 1997; Blasi, 2002]. A peptide-epitope of uPAR, AVTYSRSRYLEC [SEQ ID NO: 9], located in the region linking domain D1 to D2, is endowed with chemotactic activity and is exposed by the binding of uPA or by proteolytic cleavage. Recombinant fragments of uPAR containing at least the SRSRY [SEQ ID NO: 10] sequence ("activated" uPAR) induce migration in uPAR-lacking cells (Resnati, 1996, Fazioli, 1997). Synthetic peptides containing at least the SRSRY [SEQ ID NO: 10] sequence can efficiently substitute for uPA-u PAR interactions or for the addition of exogenous activated uPAR fragments [Resnati, 1996] [Fazioli, 1997]. However, the entire epitope is 100-1000 fold more potent indicating that the AVTY [SEQ ID NO: 11] sequence is of particular significance for the activity. Activated uPAR or chemotactically active soluble uPAR fragments are in fact able to directly activate receptors of the FPR family, notably FPRL1 and FPR [Resnati, 2002] [Selleri, 2004]. Therefore, the binding of uPA to uPAR transforms the latter into a ligand for G protein-coupled receptors.

uPAR is also directly involved in the pathogenesis and malignancy of cancer. Soluble uPAR (suPAR) was first found in the blood and ascitic fluid of ovarian cancer patient and subsequently in tissues, blood or even urine of many other types of cancer including leukemias [Pedersen, 1993] [Mizukami, 1995], [Stephens, 1999] [Mustjoki, 2000] and mammary, lung, bladder renal, prostate, cervical, ovarian carcinomas, gastric cancer, soft tissue sarcomas and tumors associated with a high rate of metastasis in particular.

In most cases, high levels of released uPAR (suPAR) are strongly related to poor prognosis [Sier, 1998; Sier, 1999] [Stephens, 1999]. Release of soluble UPAR was also observed in infectious diseases. Infection of cells by *Borrelia burgdorferi, Salmonella typhimurium* and *Streptococcus pyogenes* releases suPAR [Coleman, 2001] [Florquin, 2001]. suPAR is drastically increased in the blood and in the cerebrospinal fluid of AIDS patients [Sidenius, 2000] and in rheumatoid arthritis [Slot, 1999; Cerinic, 1998; Braat, 2000], again its level being directly related to prognosis. Therefore the invention may also be useful in other uPA-associated diseases such as gastric and intestinal diseases like inflammatory bowel disease, Morbus Crohn, premalignant colon adenomas, septic arthritis, osteoporosis, cholesteatomie, skin-and eye-diseases such as age related macula degeneration, viral and/or bacterial infections and other diseases as mentioned in european patents EP 0 691 350, EP1 182 207 and in the US-patent U.S. Pat. No. 5,712,291 which are incorporated herewith by reference in whole.

A release of suPAR and activated suPAR fragments is also observed during G-CSF-induced mobilization of hematopoietic stem cells (HSC). In this case, evidence is available indicating that suPAR fragments or synthetic peptides act as chemoattractants for human HSC [Selleri, 2004].

The Chemotactic Region of uPAR

In addition to full length suPAR fragments of suPAR are often found in cancer tissues and in cell lines. The cleavage occurs in the linker region between domain D1 and D2 [Hoyer-Hansen, 1992; Hoyer-Hansen, 1997], i.e. the region specifically endowed with chemotactic activity [Resnati, 1996] [Fazioli, 1997] [Blasi, 1997]. Different proteases can cleave uPAR, including uPA, elastase, cathepsin G and Matrix Metalloproteases [Andolfo, 2002] [Hoyer-Hansen, 1997] [Beaufort N, 2004]. Whether these fragments of uPAR contain at their N- or C-termini in part in whole the AVTYSRSRY [SEQ ID NO: 13] chemotactic epitope is not known. Of the enzymes that can cleave uPAR in this region, uPA, being the high affinity ligand for uPAR, has particular relevance, since it produces the most potent of the chemotactic fragments containing the sequence AVTYSRSRY [SEQ ID NO: 13].

This is an important question, since some of the fragments which are produced in vivo may in fact be "activated" uPAR molecules [Sidenius, 2000]. Their production in a given tissue can profoundly change the migratory potential of the cells present in that tissue. In fact, they can both directly stimulate migration [Resnati, 1996] [Fazioli, 1997] [Resnati, 2002], as well as desensitize cells to the action of other chemokines [Furlan, 2004]. While their function is not fully established, it is clear that these molecules can have a different impact if they are secreted and released into circulation or if they are kept on the cell surface. One can envisage both a negative and a positive regulation of migration of either inflammatory, hematopoietic stem or neoplastic cells. Moreover, the loss of domain D1 entails a loss of regulation by uPA [Hoyer-Hansen, 1992], producing a constitutively activated molecule directly affecting cell migration [Blasi, 2002].

This is particularly important in cancer, since released uPAR fragments have been found at low levels in the urine of normal individuals and at high levels in diseases such as leukemia (urine and blood) [Mustjoki, 2000], cancer (urine and tissues but not blood) [Sier, 2004], AIDS [Sidenius, 2000] and HSC mobilization [Selleri, 2004]. In addition, cell surface uPAR fragments have been demonstrated in human tumors and in cultured tumor cells [Hoyer-Hansen, 1992] [Sidenius, 2000].

The chemotactic activity of uPAR fragments, as defined in the patent application WO 98/42733, may have important repercussions on the migration of cancer and inflammatory cells. Moreover, since the mobilization of hematopoietic stems cells, or of endothelial progenitor cells depends on their migration and on their response to specific migratory signals, the chemotactic activity of uPAR fragments can be directly involved in their mobilization or contribute to regulate their mobilization [Selleri, 2004].

The fact that "active" u-PAR fragments are generated in vivo, and that their level is increased in several diseases as well as therapeutic conditions (i.e. during stem cells mobilization with G-CSF) suggests that they are part of a stimulated migration mechanism. Therefore, it would be important to evaluate the presence of the chemotactic epitope in these fragments, which today cannot be evaluated except than by complex methods involving protein purification and sequencing. Clearly, an easy detection systems of "activated" uPAR fragments and their quantitative measurement would allow evaluating the activation state of uPAR in disease and under migration-promoting conditions. This can be used to monitor the presence of migration-regulating uPAR fragments and to identify inhibitory compounds suitable for a specific therapy. In particular, an antibody-therapy would be very promising for these purposes.

Therefore, the technical problem underlying the present invention was to provide monoclonal antibodies and methods for identifying and quantitatively assess the presence of "activated" uPAR fragments in tissue or cell extracts, in biological fluids or in cell culture media. The solution to said technical problem is achieved by providing the embodiments characterized in the claims. Finding of antibodies with unique specificity for the chemotactic epitope was difficult, required repeated immunization and strategical boostings of the animals and was overall extremely inefficient. In a total of three immunizations resulting in far more than one hundred clones, only hybridomas producing antibodies of the desired specificity were found.

Accordingly, the present invention relates to a monoclonal antibody, a fragment or an immunological equivalent thereof, specific for the chemotactic epitope of the activated uPAR. The present invention describes the production of monoclonal antibodies against activated uPAR fragments comprising the chemotactic epitope. In particular, preferred monoclonal antibodies of the present invention are 13E11, 14C4, 13A6, 1C5, 2A8, 4E11, 5F1, 7G9 and 8E3, a fragment or an immunological equivalent thereof. Most preferred monoclonal antibodies of the present invention are 7G1 and 8D3, a fragment or an immunological equivalent thereof. The monoclonal antibodies of the present invention are able to specific recognize in whole or in part the peptide epitope of uPAR, being the AVTYSRSRYLEC [SEQ ID NO: 9] sequence which is the sequence comprising amino acid position 84-95 of uPAR and linking the domain D1 and D2 of uPAR.

In the context of the present invention, the term "chemotactic epitope" of activated uPAR is therefore represented by the whole or a part of the chemotactic peptide of uPAR. The minimal sequence which is recognized by the monoclonal antibody of the present invention is therefore the minimal chemotactic epitope represented by the sequence SRSRY [SEQ ID NO: 10]. This is the minimal epitope the uPAR fragment has to contain to be in the "activated" form and therefore to be a migration-regulating or inducing uPAR fragment. As further preferred, the monoclonal antibodies of the present invention recognize an epitope which contains the most potent part of the chemotactic peptide, having a sequence length of 4 amino acids of the sequence AVTY [SEQ ID NO: 11] or which consists of a part of the chemotactic peptide AVTYSRSRYLEC [SEQ ID NO: 9] having a minimum sequence length of 6 amino acids whereof 5 consist of the sequence SRSRY [SEQ ID NO: 10]. The sequence which is recognized as an epitope can include further contiguous amino acid units of the carboxy terminus of the chemotactic peptide of uPAR, i.e. including SRSRYLEC [SEQ ID NO: 12]. Thus the epitope sequence can include a stretch of 4-12 contiguous amino acids of the AVTYSRSRYLEC [SEQ ID NO: 9] sequence, in particular, a stretch of at least 5, preferably at least 6, contiguous amino acids thereof. In a preferred embodiment, the monoclonal antibodies of the present invention are capable of specifically recognize the activated uPAR D2D3$_{84-274}$ fragment. In a further preferred embodiment the monoclonal antibodies are capable of recognizing the chemotactic epitope AVTYSRSRY [SEQ ID NO: 13], being the amino acid sequence stretch 84-92 of the uPAR.

A very important aspect of the present invention is that the monoclonal antibodies obtained by the present invention are unable to recognize intact, full-length suPAR. Further, the monoclonal antibodies of the present invention are unable to recognize uPAR fragments with amino terminus YLEC [SEQ ID NO: 17], LEO [SEQ ID NO: 18], or upward, i.e. uPAR fragments consisting of peptides D2D3$_{92-274}$, D2D3$_{93-274}$ and upward. The amino acid residues 93-96 have no function in the chemotactic activity of uPAR. The monoclonal antibodies of the present invention preferably bind/are highly specific to chemotactically active uPAR or active fragments thereof. Further according to the invention the affinity of the monoclonal antibodies to soluble full length uPAR is preferably at least 3-4 fold less than for active fragments. In contrast thereto, antibodies of the state of the art recognize all uPAR fragments and are not able to distinguish between chemotactically active and not chemotactically active fragments.

In particular, the monoclonal antibodies bind to uPAR fragments which are formed in tumor tissue, e.g. by enzymes which are present in tumor tissue.

Since the antibodies disclosed in EP 691 350, in particular, the antibodies produced by the hybridoma cell lines 1.H2.10A3 and 1.C8.26A3 bind also to full length uPAR, they do not fall under the present invention but are disclaimed therefrom.

Since the antibodies of the present invention specifically bind chemotactically active uPAR fragments and, in particular, recognize the chemotactic region SRSRY [SEQ ID NO: 10] (minimal chemotactic epitope), which is only accessible at activated uPAR, they are useful, in particular, for the selective analysis or detection of the presence of activated uPAR in mixtures containing various uPAR molecules, in particular, full length uPAR and/or differently cleaved uPAR such as proteolytically cleaved uPAR.

Antibodies which also bind to full length or non-chemotactically active uPAR such as the antibodies described in EP 691 350 cannot differentiate between activated and non-activated uPAR and are therefore not suitable for that task.

These properties represent a substantial advantage and difference over existing antibodies which, in addition to some fragments, all recognize also the full-length suPAR. Moreover, available antibodies, while able to detect the presence of uPAR or suPAR fragments in tissues and biological fluids, are unable to reveal (and/or to quantitate) whether these fragments are biologically active, i.e. whether they do or do not contain the chemotactic epitopes. The antibodies presented in this application, therefore, represent a substantial step forward in the provision of new antibodies useful in diagnostics, prognostics and therapy.

Compared to polyclonal antibodies, the monoclonal antibodies of the invention offer a considerably improved affinity and selectivity.

A further significant characteristic of the monoclonal antibodies of the present invention is their ability to detect with high precision a very small antigen concentration. In particular, the monoclonal antibodies are capable of specifically determining an antigen dose of at least 0.30 ng/ml, preferably at least 0.250 ng/ml. The preferred minimum detectable dose of the antigen detected via immunofluorometric assay by the monoclonal antibodies of the invention is at least 0.125 ng/ml, more preferred at least 0.0125 ng/ml and most preferred at least 0.00125 ng/ml. However, the assay can be easily increased in sensitivity using methods known to experts in the field, like time-resolved fluorescence with europium labeling.

The monoclonal antibodies of the invention are highly specific for activated uPAR fragments. In particular, the monoclonal antibodies have a specificity to the fragment $D2D3_{84-274}$, which is preferably at least 3, in particular, at least 20, preferably at least 50, more preferably at least 70 fold higher and even more preferably at least 100 fold higher than for the $D2D3_{93-274}$ fragment under the conditions as described in Example 3.

A still further feature of the monoclonal antibodies of the present invention is their capability of blocking cell migration. The inhibitory activity on cell migration is according to the findings of the present invention at least 30%, more preferably at least 40%, even more preferably at least 50%, under the conditions as described in Example 5.

The monoclonal antibodies of the present invention may be prepared using any technique that provides for the production of antibody molecules by continuous cell lines in culture. As shown in Example 1, a host animal is immunized by injection with the synthetic peptides corresponding to the chemotactic epitopes as described above, which show immunogenic properties. The host animal can include goats, rabbits, rats, mice, humans and others. In particular, the host is a mouse as shown in Example 1. Depending on the host species, various adjuvants may be used to increase immunological response. The techniques which provide the production of antibody molecules by continuous cell lines in culture, include, but are not limited to, the hybridoma technique, the human bi-cell hybridoma technique and the EBV-hybridoma technique (Köhler, G. et al. (1975) Nature 256: 495-497; Kozbor D. et al. (1985) J. Immunol. Methods 81: 31-42; Cote R. J. et al., Proc. Natl. Acad. Sci. 80: 2026-2030; Cole S. P. et al. (1984), Mol. Cell Biol. 62:109-120). Suitable cells for the production of the antibodies of the present invention are eukaryotic cells, mammalian cells, hybridoma cells or CHO cells.

The specific monoclonal antibodies 13E11, 14C4, 13A6, 1C5, 2A8, 4E11, 5F1, 7G1, 7G9, 8D3 and 8E3 are preferred examples of antibodies. Particularly preferred are 7G1 and 8D3. These antibodies of the present invention are produced by the hybridoma cell line 7G1/87 (clone 42) which was deposited on Mar. 2, 2005 at Deutsche Sammlung von Mikroorganismen and Zellkulturen GmbH (DSMZ, 38124 Braunschweig, Mascheroder Weg 1b, Germany) with the Accession No. DSM ACC2716 and the hybridoma cell line 8D3/18 which was deposited on Mar. 2, 2005 with the Accession No. DSM ACC2717 under the terms and conditions of the Budapest Treaty.

The monoclonal antibodies of the present invention can be used as whole antibody molecule or as active fragments of said monoclonal antibody. An active fragment as used herein denotes an antibody fragment which contain specific binding sites for the chemotactic epitope of activated uPAR and which therefore presents the same biological specificity of the monoclonal antibody itself. For example, such fragments include, but are not limited to the $F(ab)'_2$ fragments which can be produced by pepsin digestion of the monoclonal antibody of the present invention and the F(ab) fragments which can be generated by reducing the disulfide bridges of $F(ab)'_2$ fragments.

In a most preferred embodiment of the invention an active fragment capable of specifically recognizing the chemotactic epitope of activated uPAR comprises the CDR-sequence portion of monoclonal antibody 7G1 and/or 8D3 (see FIG. 14).

In addition, genetically modified monoclonal antibodies can be prepared according to the present invention using methods well known in the art (Morrison, S. L. et al. (1984) Proc. Natl. Acad. Sci. 81:6851-6855; Neuberger, M. S. et al. (1984) Nature 312:604-608; Takeda, S. et al. (1985) nature 314:452-454), and they are denoted herein as immunological equivalents of the monoclonal antibody. In particular, the invention also relates to genetically modified antibodies which can be selected from chimeric antibodies, partially or fully humanized antibodies, single chain antibody or short-chain antibody fragments, as long as they are able to bind the whole chemotactic epitope of activated uPAR or fragments thereof as described above. Therefore, at least the CDR-regions or parts thereof, conferring the specific binding ability have to be maintained in such genetically modified monoclonal antibodies.

Especially preferred are polypeptides which contain the amino acid sequence of the variable region of the heavy and light chains of the monoclonal antibodies 13E11, 14C4, 13A6, 1C5, 2A8, 4E11, 5F1, 7G1, 7G9, 8D3 and 8E3 and particularly preferred of 7G1 or 8D3.

The invention further concerns nucleic acids, which encode antigen-binding sites (paratopes) of the light and/or heavy chains of the monoclonal antibodies which show a selective affinity to the chemotactic epitope of uPAR. Particularly preferred are nucleic acids which encode the antigen-binding sites of the light and/or heavy chains of the monoclonal antibodies 7G1 and/or 8D3. More preferred are nucleic acids, the sequences of which encode the CDR-regions of the light and/or heavy chains of the monoclonal antibodies 7G1 and/or 8D3. Most preferred are nucleic acids, the nucleotide sequences of which encode the amino acid sequences of the variable regions of the light and/or heavy chains of the monoclonal antibodies 7G1 and/or 8D3 (as shown in FIG. 14).

Due to the diversity of the genetic code, the nucleic acids mentioned herein comprise all DNA and/or RNA molecules the nucleotide sequence of which can be translated in the mentioned amino acid sequence by using one of the known codon usages. The nucleic acids according to the invention can be modified, e.g. via methylation in a manner that said nucleic acids can be translated both in vivo and in vitro to functional polypeptides or proteins, which show a selective affinity to the chemotactic epitope of uPAR. The invention further refers to all nucleic acids, the expression of which leads to polypeptides and/or proteins wherefrom compositions result after a covalent and/or non-covalent linkage and/or posttranslational modification with other molecules representing an immunologic equivalent to the monoclonal antibodies of the invention. In one embodiment of the invention, the said nucleic acids are integrated into a suitable vector-expression system, so that monoclonal antibodies directed against the chemotactic epitope of uPAR or immunological equivalents of these antibodies are produced.

Furthermore, according to the present invention, the monoclonal antibody can be linked to a label or an effector. Suitable labels which may be used include radionucleides, enzymes, fluorescent, chemiluminescent or chromogenic agents as well as substrates, cofactors, inhibitors, magnetic particles and the like.

The presence of activated uPAR fragments in a biological sample can be determined according to the present invention by immunological methods using the above-described monoclonal antibodies. Therefore, a further aspect of the present invention is a method for the detection and/or the is quantitative assessment of activated uPAR $D2D3_{84-274}$ and/or fragments thereof which comprise the chemotactic epitope in biological samples comprising the steps of
a) providing a sample to be tested
b) bringing the sample into contact with the monoclonal antibody, a fragment or immunological equivalent thereof, and
c) detecting and/or quantitatively assessing the binding of the monoclonal antibody, the fragment or the immunological equivalent thereof, to components of the sample.

Preferred examples of such methods include enzyme-linked immunoadsorbent assay (ELISA), immunofluorometry, time resolved fluorescence with europium labeling, immunofluorescence, cytofluorometry, immunoblotting and immunoproliferation assays.

The above described method of the present invention allows it to identify and in particular to quantitatively assess in absolute and personal terms the presence of the above-described activated forms of UPAR, in particular $D2D3_{84-274}$, in biological samples. Suitable biological samples are in particular tissue or cell extracts, serum, blood, urine, other biological fluids and cell culture media. This method is in particular efficient in determining the cleaved uPAR concentrations, i.e. the concentration of fragments containing the chemotactic epitope and therefore being able to stimulate the migration mechanism. Therefore, the method according to the present invention is used for evaluating the activation status of uPAR in diseases. More in particular, the method of the present invention is used for evaluating the activation status of uPAR under cell migration-promoting conditions.

This method will not only be valuable in diseases in which excess migration occurs (cancer, among others) in which high levels of suPAR is a well-known negative prognostic marker, but also in cases in which the extent of cell migration is not sufficient, like in some patients that do not respond to regimens designed to mobilize hematopoietic stem cells.

Since the method of the present invention is able not only to identify the presence of chemotactic fragments of uPAR, but, thanks to the high specificity of the monoclonal antibodies to said chemotactic fragments, also to quantify the activated uPAR fragments in biological samples, it is in a very suitable manner used for the prognosis and diagnosis of conditions of diseases which are associated with uPAR and especially with high levels of uPAR fragments. Diagnostic assays include methods which utilize the monoclonal antibodies and a label to detect the chemotactic uPAR fragments in human body fluids, extracts of cell or tissues or cell culture media. The monoclonal antibodies may be used with or without modification and may be labelled by joining them either covalently or non-covalently with a reporter molecule. In particular, the method according to the present invention is suitable for cancer prognosis and diagnosis. Further, the method of the present invention can be used for monitoring an anti-cancer therapy.

The monoclonal antibody of the invention, fragments or immunological equivalents thereof may further be useful in diagnostic applications, wherein the presence or amount of the activated uPAR fragments are to be assessed, Hence, a further aspect of the invention is a diagnostic composition comprising as active ingredient a monoclonal antibody, a fragment or immunological equivalent thereof, as defined above or a combination thereof.

Further, the monoclonal antibodies of the present invention that bind immunospecifically to the chemotactic epitope of uPAR or to fragments thereof may be also used in therapeutic methods. A particularly preferred embodiment of the present invention therefore relates to a pharmaceutical composition comprising as active ingredient a monoclonal antibody, a fragment or immunological equivalent thereof, as defined above or a combination thereof.

Pharmaceutical compositions suitable for use in the invention include compositions wherein the active ingredients are contained in an effective amount to achieve the intended purpose. The determination of an effective dose is well within the capability of those skilled in the art. In addition to the active ingredient, these pharmaceutical compositions may contain suitable pharmaceutically acceptable carriers comprising excipients, auxiliaries, which facilitates processing of the active compound into preparations, which can be used pharmaceutically. Further details on techniques for formulation at administration may be found in the latest edition of Remington's Pharmaceutical Science (Maack Publishing Co., Easton, Pa.). Such pharmaceutical compositions may be administered to a patient alone or in combination with other agents or drugs. The pharmaceutical composition of this invention may be administered by any number of routes including, but not limited to, oral, intravenous, intramuscular, intraarterial, intramedullary, intrathecal, intraventricular, transdermal, subcutaneous, intraperitoneal, intranasal, enteral, topical, sublingual or by rectal means.

A particularly preferred embodiment of the present invention is the use of a monoclonal antibody according to the present invention for the preparation of a pharmaceutical composition for the inhibition of the cellular activity of activated uPAR fragments, in particular uPAR $D2D3_{84-274}$. More preferably, the use of the monoclonal antibody according to the present invention is aimed for blocking cell migration and even more particularly for blocking urokinase and/or uPAR dependent cell migration.

The monoclonal antibody may further by conjugated with other therapeutic agents acting in this way as a targeting or delivery mechanism for bridging the therapeutic agent to cells or tissue which express activated uPAR. Preferably the monoclonal antibody is conjugated with a cytostatic agent.

A very important aspect of the present invention is the use of the monoclonal antibody for the preparation of a pharmaceutical composition for the treatment, prevention and/or diagnosis of diseases associated with activated uPAR. In particular, the monoclonal antibodies are suitable for the treatment, prevention and/or diagnosis of cancer metastasis, cancer invasion, leukemias, acute inflammatory disorders, chronic inflammatory disorders, AIDS, AIDS dementia complex and infectious diseases.

In connection with the treatment of uPAR-associated diseases, an aspect of the present invention relates also to the combined and/or conjugated administration of the highly specific monoclonal antibodies together with other therapeutic agents or other uPA/uPAR inhibitors, as well as in combination with radiation therapy and surgery. Preferred uPA/uPAR inhibitors are for example 3-amidino or 3-guanidino phenylalanine derivatives as disclosed in EP-A-1098651 and WO 2004/103984, which are herein incorporated by reference.

The presence of altered levels of fragments of suPAR indicates the presence of the uPAR-associated disease. Such assays may also be used to evaluate the efficacy of a particular therapeutic treatment regime in animal studies, in clinical trials or in monitoring the treatment of an individual patient.

A still further aspect of the invention is the use of the inventive monoclonal antibody to identify compounds capable of inhibiting cellular activity of activated uPAR fragments, in particular uPAR $D2D3_{84-274}$.

Finally, the invention also relates to a reagent kit comprising the monoclonal antibody of the invention, a fragment or an immunological equivalent thereof, and further suitable reagents. The kit may be used for diagnostic or therapeutic purposes or for screening application as described above. The kit may further contain user instructions.

The Figures show:

FIG. 1 shows the schemes of the structure of suPA and its derivative constructs. $D1D2D3_{1-277}$ linker region: [SEQ ID NO: 13] was purified from the culture supernatant of stably transfected CHO cells; D2D388-277 (linker region: [SEQ ID NO: 10] was generated by cleavage of $D1D2D3_{1-277}$ with chymotrypsin and purified again with a uPAR antibody-column. $D2D3_{84-274}$ (linker region: [SEQ ID NO: 13] and $D2D3_{93-274}$ were purified from culture supernatant of transient transfected COS-7 cells with a-FLAG antibody-column. $GP1-D2D3_{84-274}$ (linker region: [SEQ ID NO: 13] and $GP1-D2D3_{93-274}$ represent the truncated forms of uPAR expressed on the cell surface (SP . . . signal peptide; GPI . . . glycosylphosphatidyl inositol).

FIG. 2 shows the results of the immunoprecipitation analysis on the soluble form of uPA fragments. The immunoprecipitation analysis was carried out using crude lysates of HEK-293 $D2D3_{84-274}$ (1) and $D2D3_{93-274}$ (2) expressing cells. They represent surface-bound uPAR fragments recognized by the antibodies employed.

Figure 5:
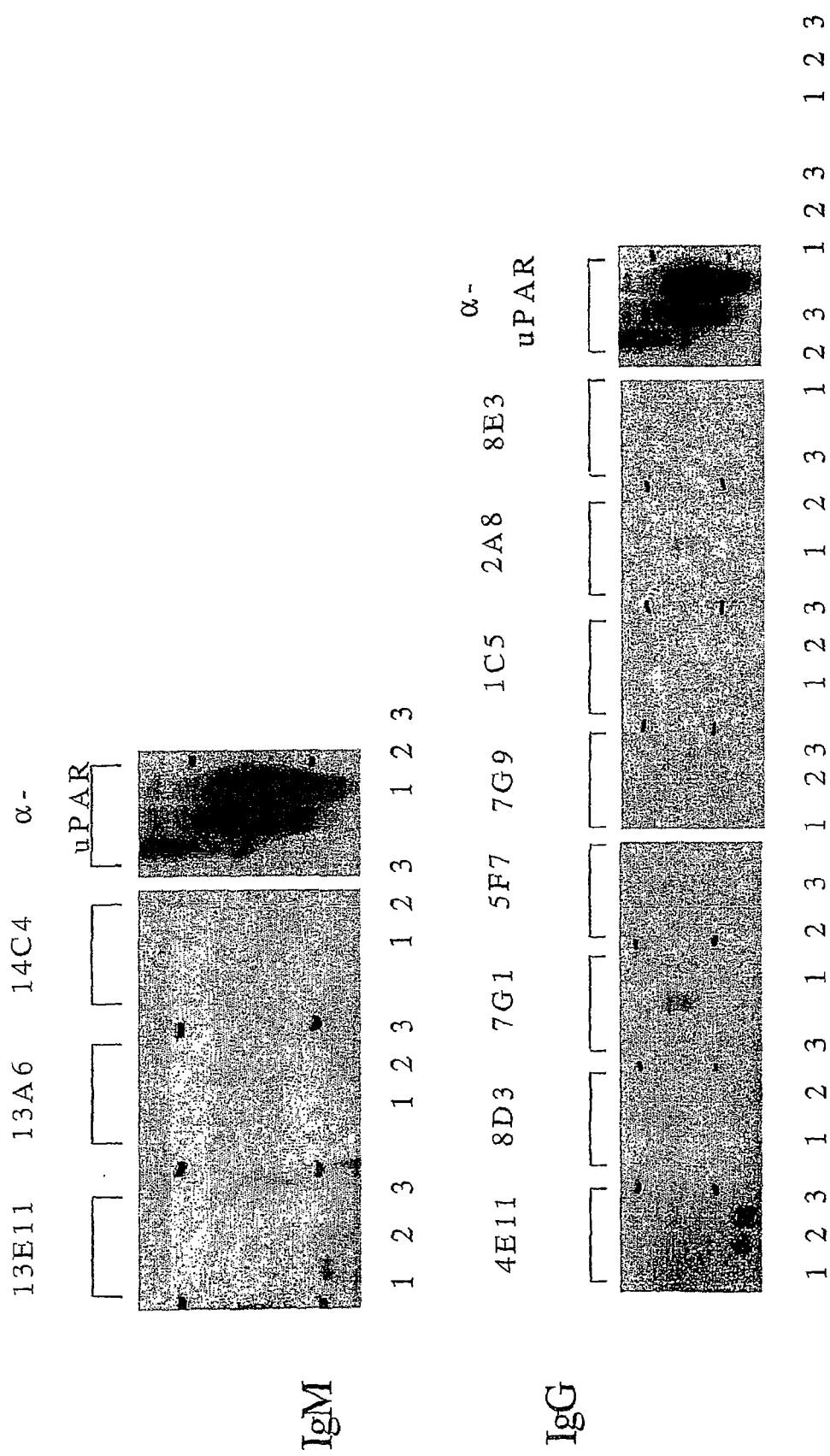

FIG. 5 shows Western blot using crude lysates (10 μg/lane) HEK-293 $D2D3_{84-274}$ (lane 2) or $D2D3_{93-274}$ (lane 3) expressing cells and HEK-293 wild type (lane 1) as a negative control. The monoclonal antibodies were diluted at 1 μg/ml in TBS containing 3% BSA.

Figure 6:
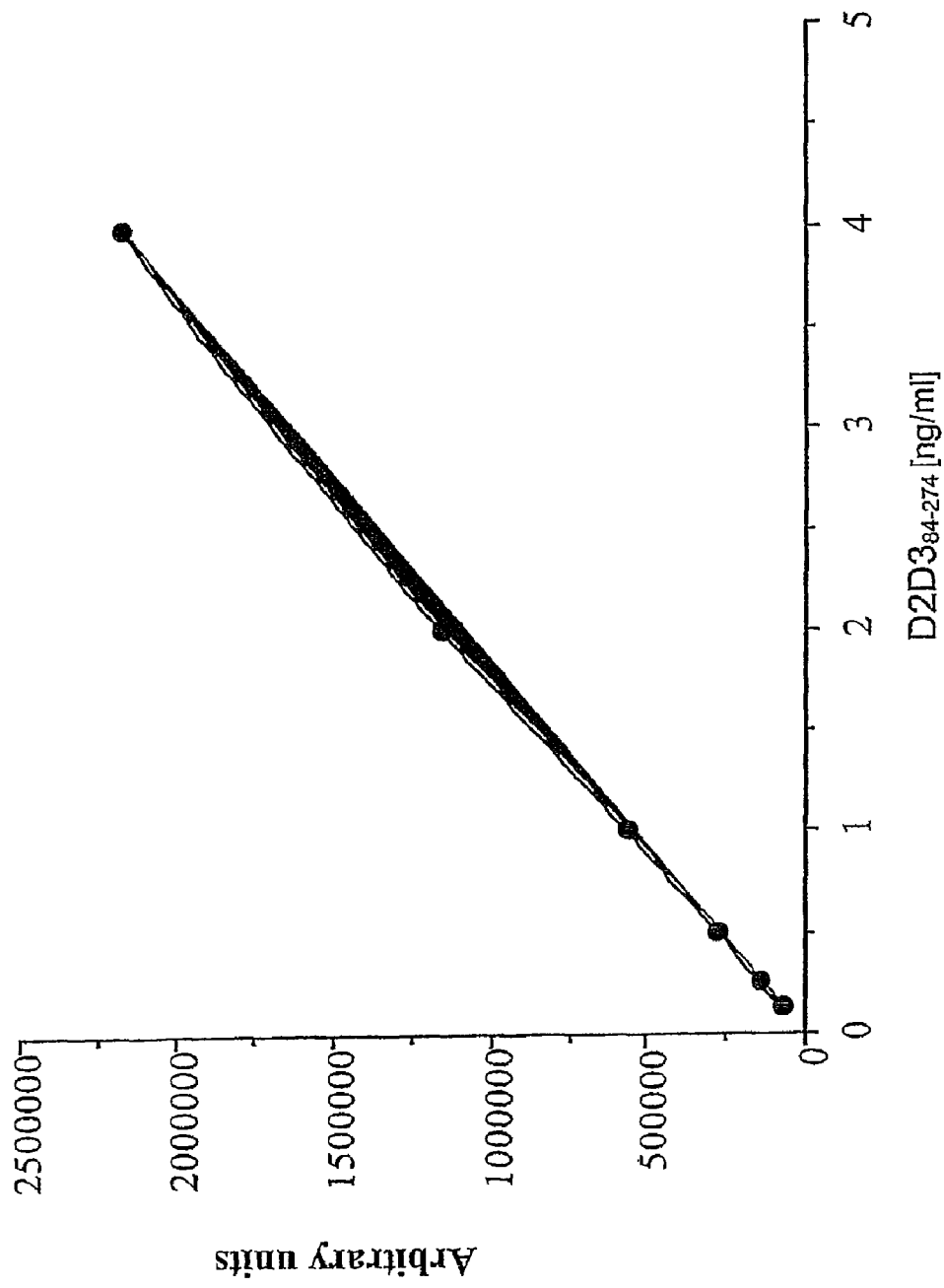

FIG. 6 shows the curve for the $D2D3_{84-274}$ immunofluorimetric assay.

Figure 7A:
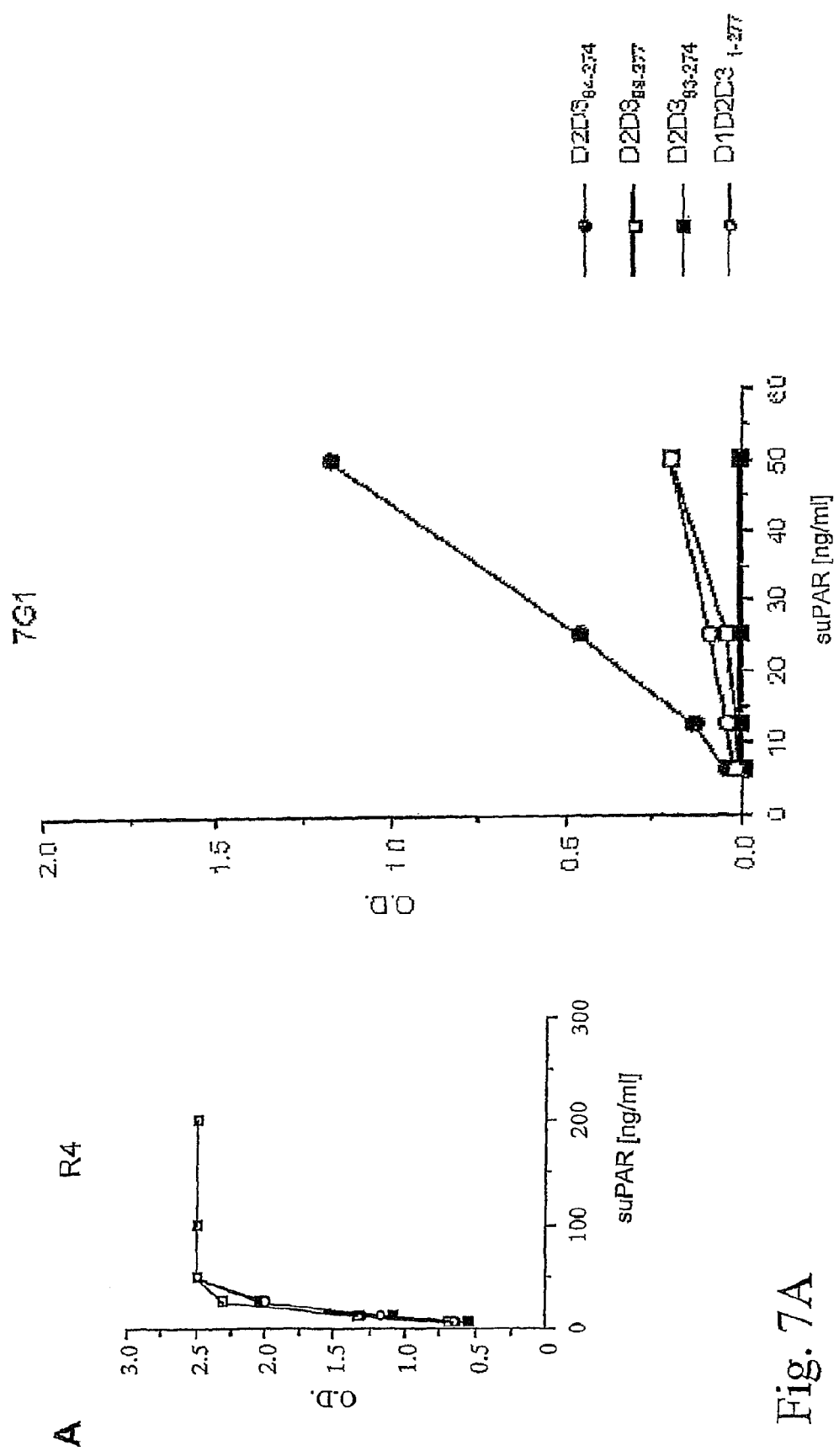

FIG. 7A shows the results of standard ELISA assay carried out using the anti-uPAR monoclonal antibody R4 as control and the anti-peptide monoclonal antibody of the present invention 7G1.

Figure 7B:
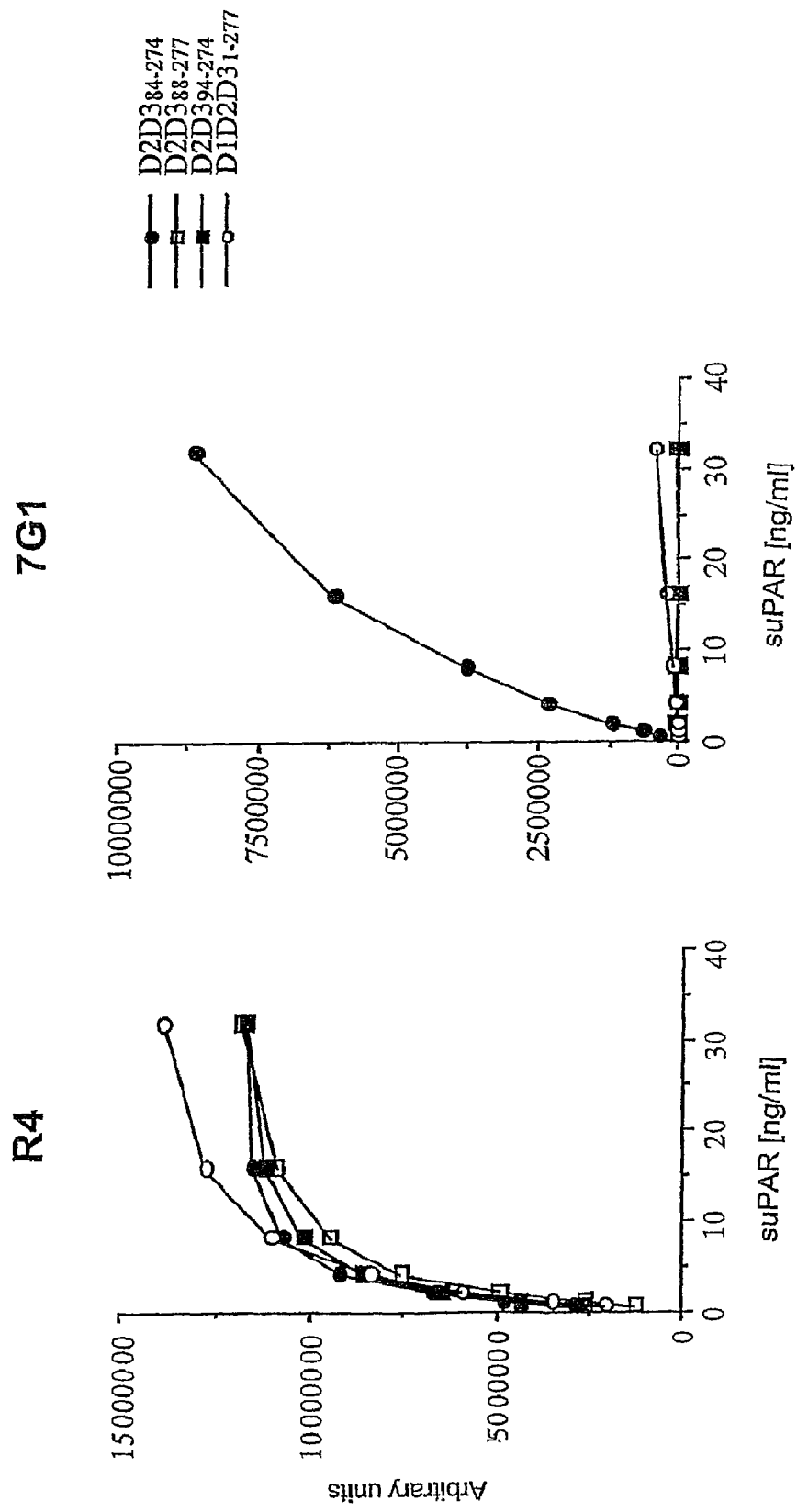

FIG. 7B shows the results of the immunofluorometric assay carried out using the anti-uPAR monoclonal antibody R4 as control and the anti-peptide monoclonal antibody of the present invention 7G1.

Figure 8:
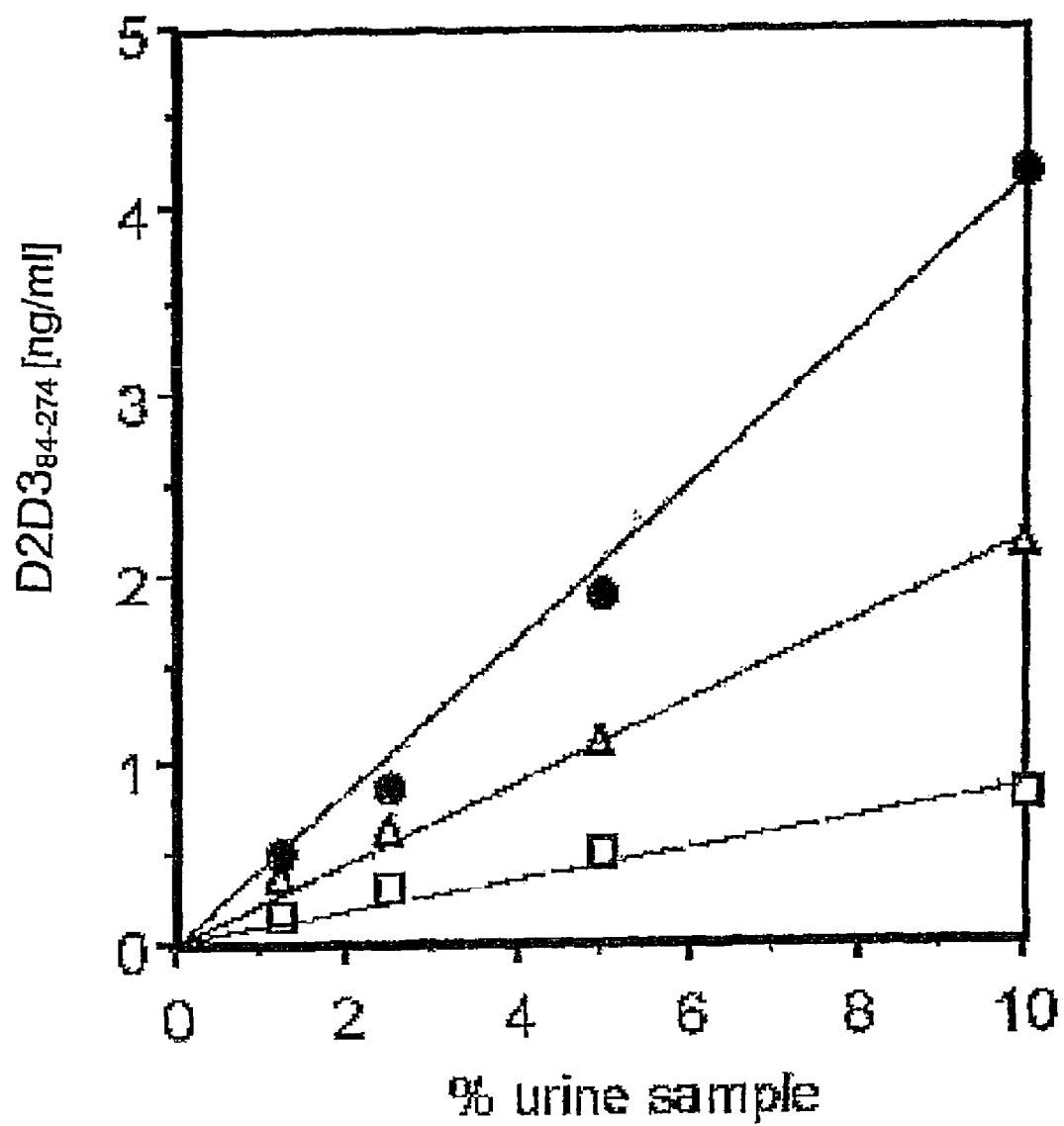

FIG. 8 shows linearity and recovery of ELISA signal from calibrator $D2D3_{84-274}$.

FIG. 8A shows the effect of dilution of three different urine samples on the respective $D2D3_{84-274}$ signals obtained.

Figure 8B:
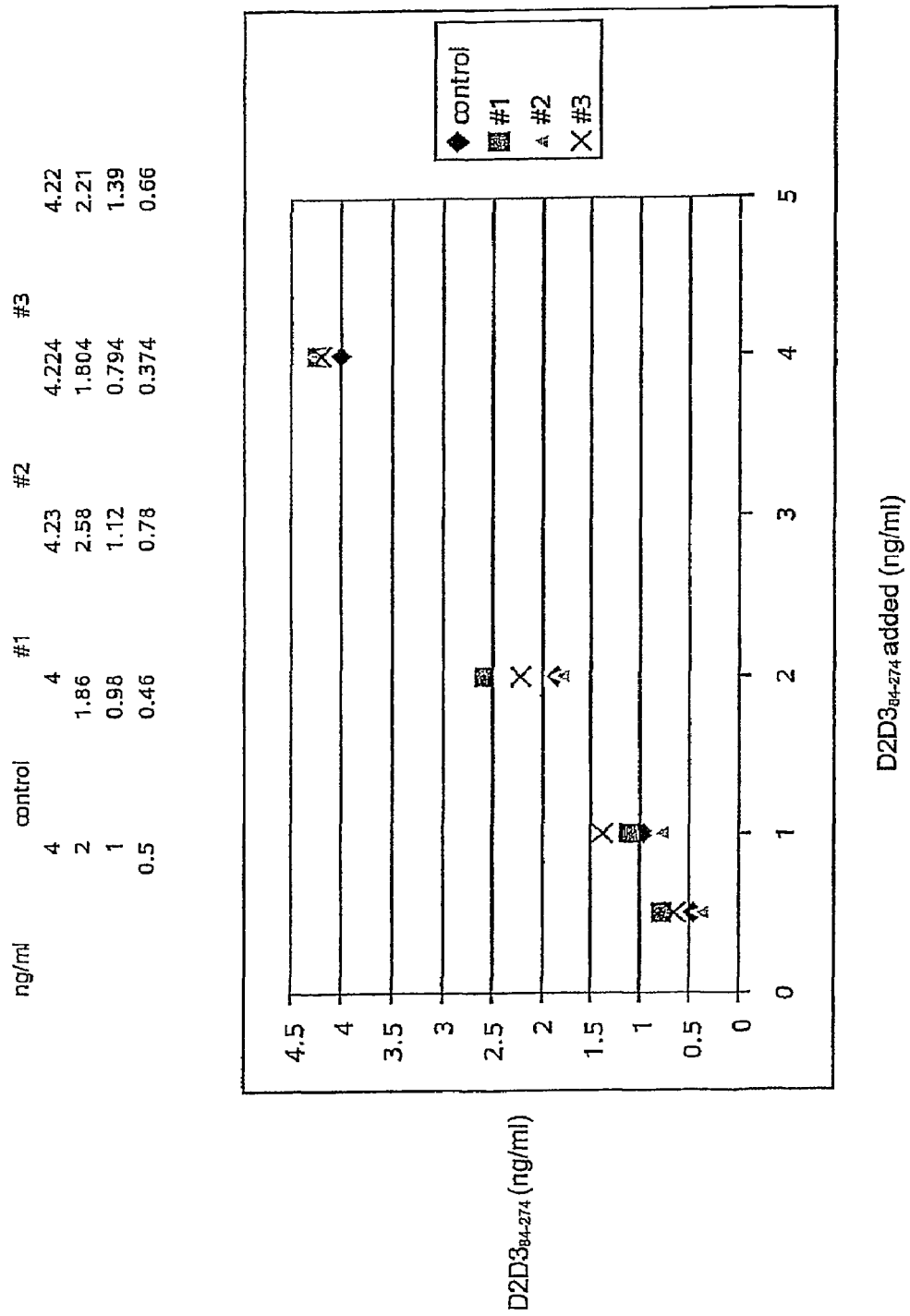

FIG. 8B shows the recovery of ELISA signal from calibrator $D2D3_{84-274}$ added in increasing concentration to assay dilution buffer (1:10 dilution of three different urine samples).

Figure 9:
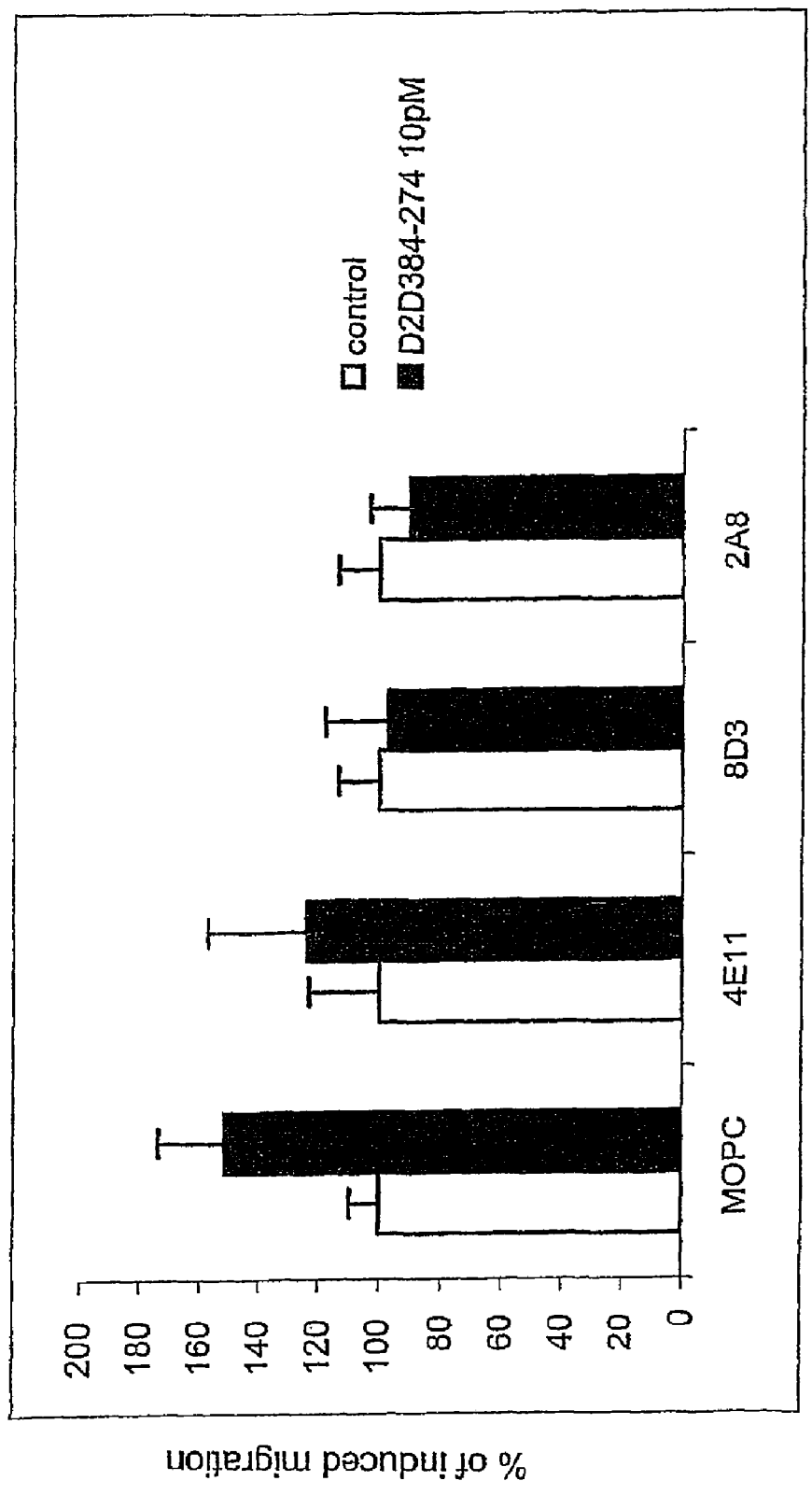

FIG. 9 shows the influence of the monoclonal antibody 8D3 on the chemotaxis of monocytes in the presence of chemoctactic active uPAR-fragments $D2D3_{94-274}$. Freshly isolated monocytes were inoculated with 10 pM of the chemotactic active uPAR-fragments. The stimulus is preincubated with the Mabs (5 μg/ml) for 20 minutes before the assay. Results represent the average of 2 experiments in triplicate.

Figure 10:
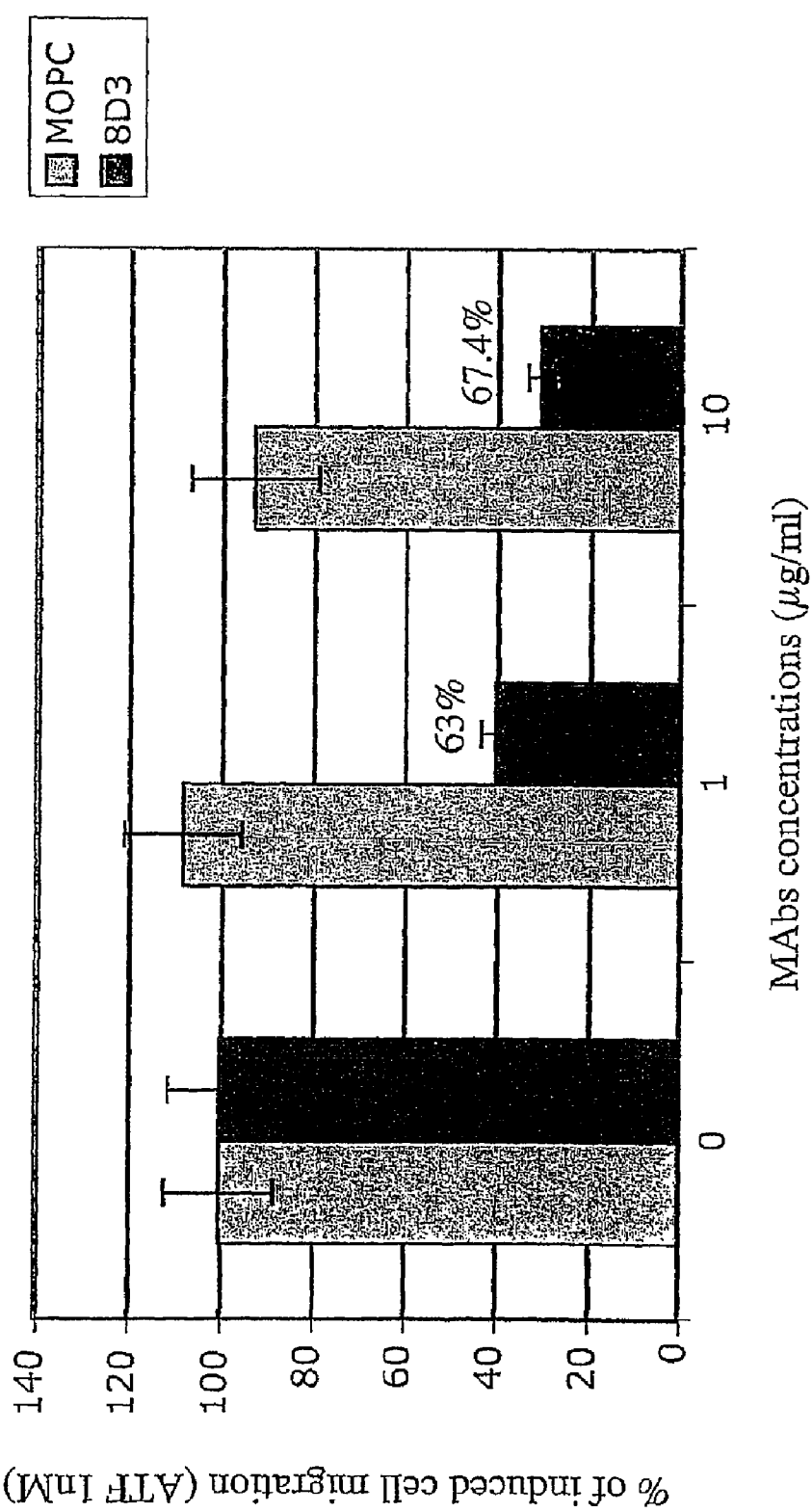

FIG. 10 shows the results of the chemotactic assay of monocytes, incubated with 1 nM ATF in the presence of different concentrations of Mab 8D3. The Mabs were added to the cells before the assay. Results represent the average of 2 experiments in triplicate. The percentage of inhibition is referred to control MOPC antibody treatment.

Figure 11:
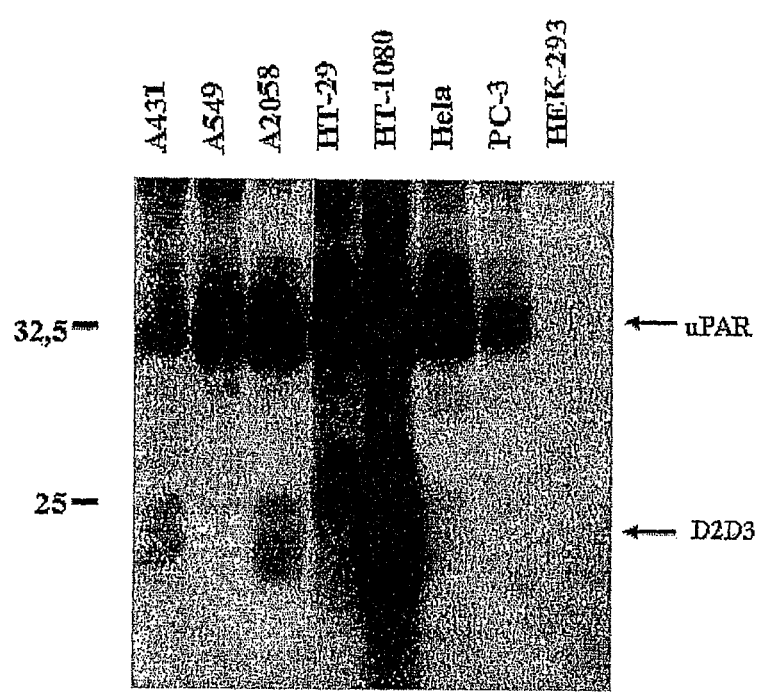

FIG. 11 shows the results of the uPAR immunoprecipitation assays of 7 different tumor cell lines and HEK-293 cells. All cell lines tested expressed uPAR.

FIG. 12A shows the inhibiting influence of the Mab 8D3 application on the proliferation of different tumor cell lines. Mab (10 μg/ml) was added to the cells the day after were plated. The cells counted after 5-7 days after seeding. The 100% of cell growth is referred to effect of control Mab (MOPC).

Figure 12B:
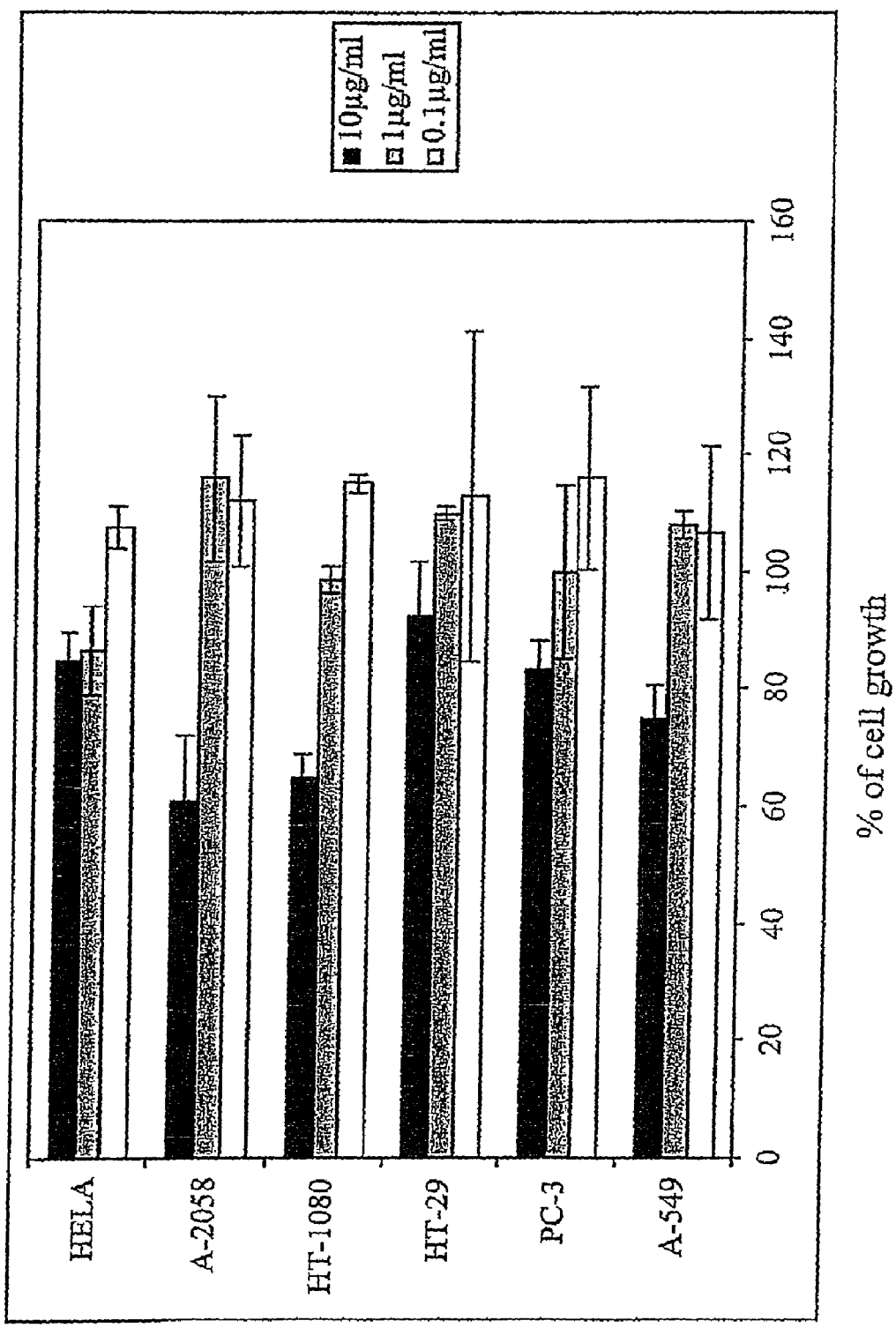

FIG. 12B shows the dose-response curve of Mab 8D3 in tumor cell growth. Different concentrations of 8D3 Mab were added to the cells the day after were plated. The cells were counted after 5-7 days after seeding. The 100% of cell growth is referred to effect of control Mab (MOPC).

Figure 13:
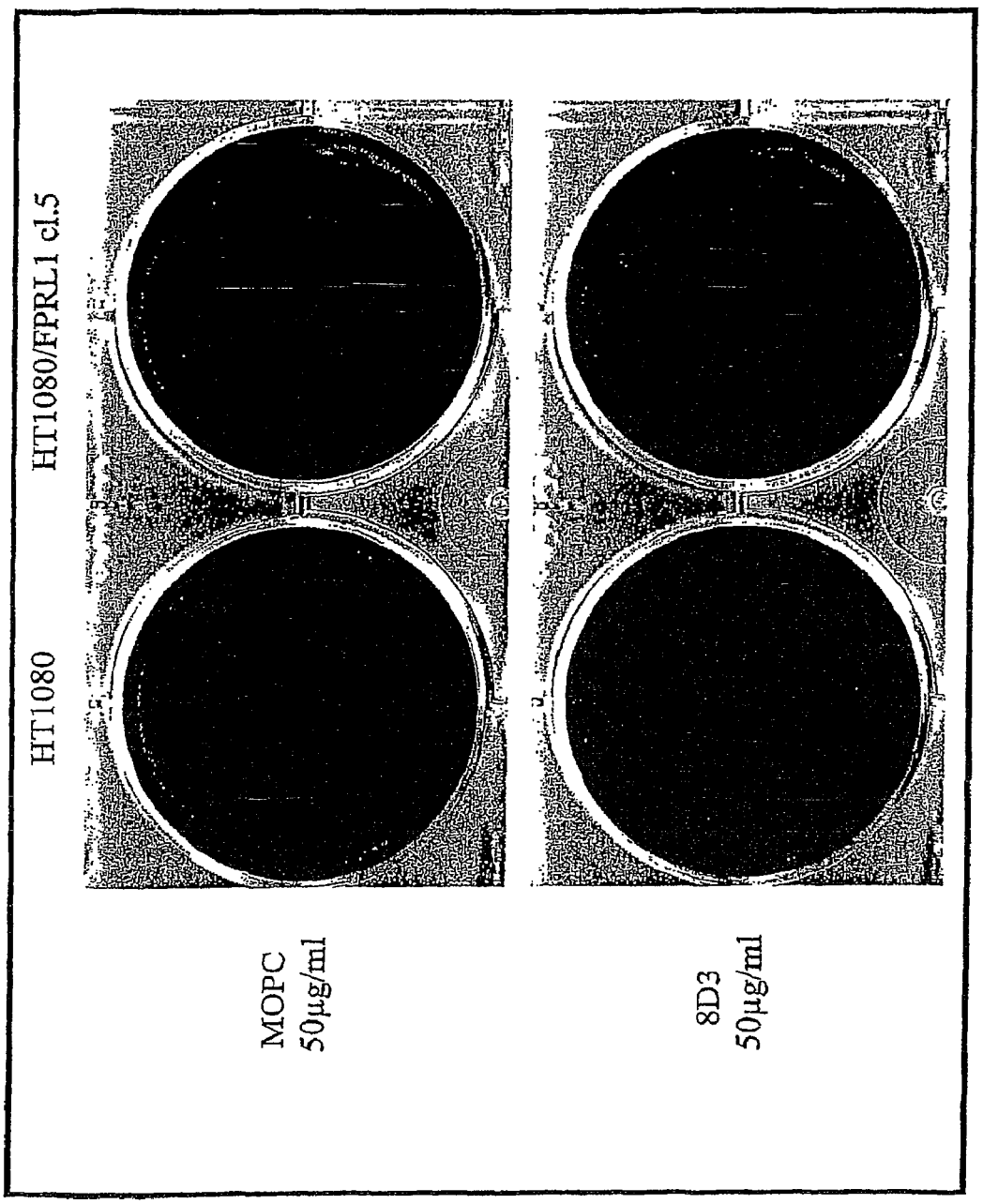

FIG. 13 shows the inhibiting effect of the treatment with the antibody 8D3 on the colony formation of tumor cell lines. Cell proliferation was performed in soft agar: Cells were suspended in 0.3% nobel agar, layered over 0.8% agar-medium base layer and treated with Mabs. After 14 days the cells were stained with nitro-blu tetrazolium.

FIG. 14 shows the nucleotide and amino acid sequences of the variable regions of monoclonal antibodies 7G1 (FIG. 14A) and 8D3 (FIG. 14B).

EXAMPLE 1

Production of Sequence-Specific Monoclonal Antibodies Recognizing the Chemotactic Epitope of uPAR 1a. Materials and Methods
a1. Mice Immunization Female BALB/c mice were immunized for a total of five minutes with a combination of three synthetic peptides (AV-TYSRSRYLEC [SEQ ID NO: 9], YSRSRYLEC [SEQ ID NO: 14], SRYLEC [SEQ ID NO: 15] derived from the linker region between D1 and D2 of uPAR, conjugated to Keyhole limpet hemocyanin (KLH). No antibody with the desired specificity was obtained. In a second immunization experiment with the same antigen as above, the animals in which the serum gave a positive result in western blot were further boosted four times (0, 14, 21 and 40 days with D2D3$_{88-277}$. In a third immunization, female BALB/c mice were injected five times (0, 14, 21, 40 and 55 days) with a combination of three synthetic peptides (AVTYSRSRYLEC [SEQ ID NO: 9], YSRSRYLEC [SEQ ID NO: 14], SRYLEC [SEQ ID NO: 15]) conjugated to Keyhole limpet hemocyanin (KLH). Briefly, 100 μg of the mixture of conjugated peptides was diluted 1:1 in complete Freund's adjuvant for the first injection and in incomplete Freund's adjuvant for subsequent injections and administered intraperitoneum three times at 2-weeks interval. Four weeks after the first immunization, the immune mouse serum did, while the preimmune serum did not react with purified proteins (D2D3$_{84-274}$ and D2D3$_{88-277}$). To generate monoclonal anti-uPAR peptide antibodies, the mice were sacrificed and their spleens removed five days after the last injection. The splenocytes were fused with NS0 myeloma cells with polyethylene glycol 1500. The fused cells were cultured in 96-well plates in DMEM containing 20% fetal calf serum, 2 mM glutamine, 2% Origen (Hyclone) and 20 μm/L HAT (hypoxanthine, aminopterin, thymidine; Sigma) at 37° C. in a 5% $CO_2$ atmosphere. The supernatants were collected and positive clones screened by ELISA immunoassay. The positive clones were expanded in flasks, tested, Ig isotyped (Ig isotype kit, Bio-Rad) and re-cloned by limiting dilution. We obtained three positive clones in the second immunization and eight in the third.

a2. Standard ELISA Method

For clones supernatants screening, immunoassay plates (Maxisorp, Nunc) were coated for 16 h at 4° C. with 100 μl/well of purified proteins (D1D2D3$_{1-277}$, D2D3$_{84-274}$ D2D3$_{93-277}$, D2D3$_{93-274}$,), 0.5 μg/ml, in 0.1 mol/l carbonate buffer, pH 9.5. The wells were rinsed three times with 300 μl/well of PBS containing 0.1% Tween 20. Wells were then treated for 30 min at 37° C. with 100 μl/well 1% BSA in PBS. The wells were washed three times with 300 μl/well of PBS containing 0.1% Tween 20. The wells were then treated for 1 h at 37° C. with 100 μl/well of hybridomas conditioned medium diluted 1:2 with PBS/1% BSA. After three washes, the wells were then incubated for 1 h at 37° C. with 100 μl/well of goat anti-mouse immunoglobulins/HRP conjugate (Amersham-Pharmacia). After three washes with washing solution, 100 μl of freshly made o-phenylendiamine dihydrochloride (OPD, Sigma-Aldrich) substrate solution (phosphate-citrate buffer, pH 5 with the addition of 10 μl $H_2O_2$ 30%) were added; after 15-20 min at room temperature, 100 μl of H2SO$_4$ 2M was added to each well and the plate was read in a microplate reader (Bio-Rad Instruments) at 490 nm.

a3. Purification of Monoclonal Antibodies

Supernatants derived from the first immunization (IgM antibodies) were purified using an immobilized mannan binding protein (Immunopure IgM purification kit, Pierce). Supernatants derived from the second immunization (IgG antibodies) were diluted two fold with Phosphate Buffered Saline (PBS, pH 7.2, Sigma) and injected into a HiTrap Protein G column (Amersham-Pharmacia). After the column was washed with PBS, the antibodies were eluted with 0.1M glycine buffer (pH 2.8). The fractions were neutralized with 1M Tris (pH9) and dialyzed over-night in PBS solution.

a4. Cell Culture

Figure 1:
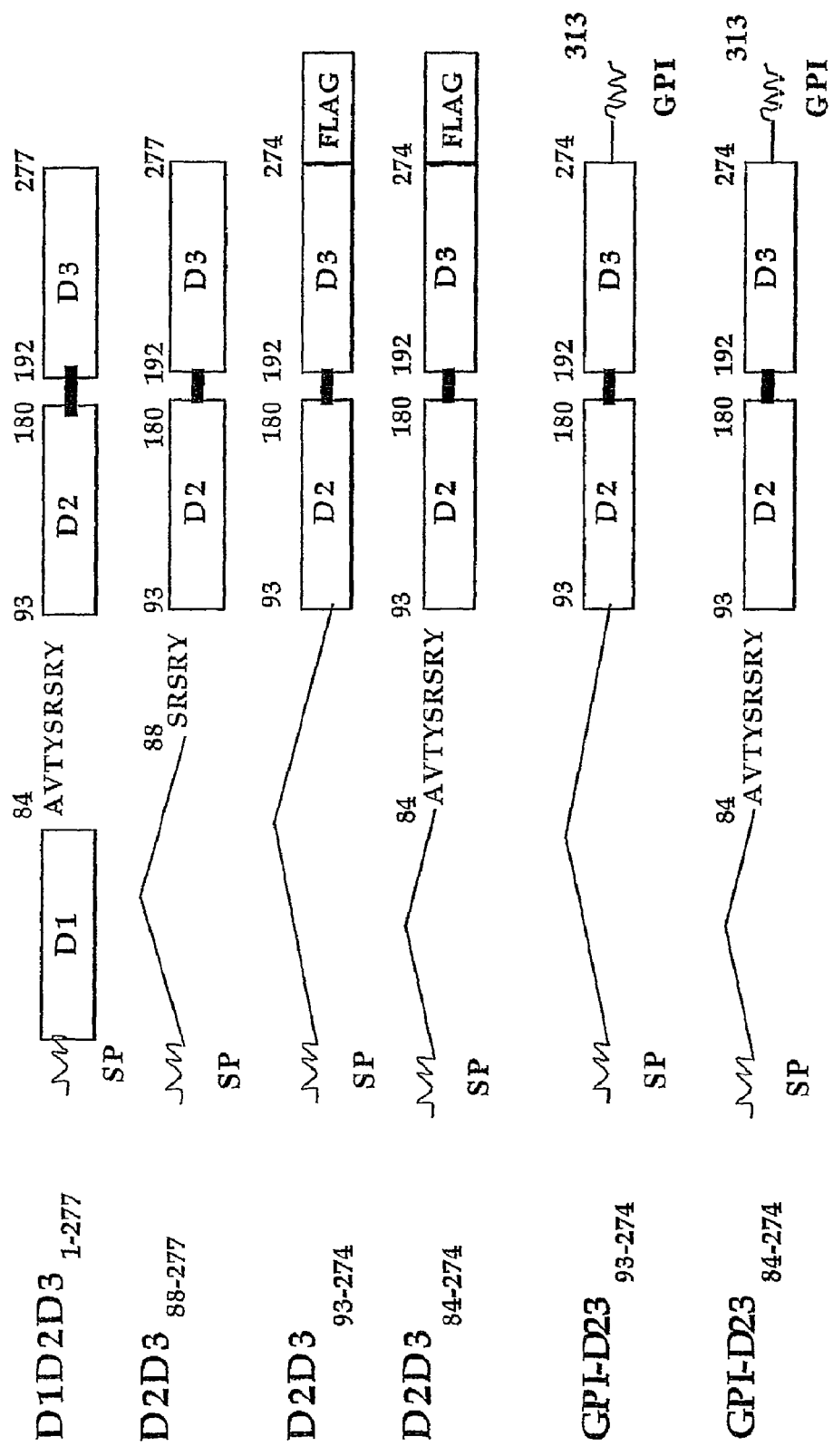

Human embrional kidney 293 (HEK-293), COS-7 and all transfected cells were grown in Dulbecco's modified Eagle's medium (Invitrogen) supplemented with 10% fetal calf serum. Transfected cells medium also contained the antibiotic G418 (0.8 mg/ml).

a5. Production of Soluble, Truncated uPAR Molecules uPAR has three domains, an N-terminal (D1), an intermediate (D2) and a C-terminal domain (D3), which is connected to the GPI anchor. Truncated molecules are identified by the number of the domains (i.e. D1, D2, D3) and by the amino acids sequence they express (i.e. D2D3$_{93-274}$, domain 2 and 3, from residue 93 to 274). Residue 1 identifies the N-terminal amino acid in the mature protein, i.e. after the removal of the signal peptide [Roldan, 1990]. The full size soluble uPAR has been previously obtained [Masucci, 1991] and is designated D1D2D3$_{1-277}$. D2D3$_{88-274}$ was generated by cleavage of D1D2D3$_{1-277}$ with chymotrypsin and purified by a-uPAR antibody-column. Mutant cDNAs encoding soluble uPAR were generated by PCR. The mutant receptors D2D3$_{84-274}$ and D2D3$_{93-274}$ were tagged at the C-terminus with the peptide sequence HRRASVDYKDDDDK [SEQ ID NO: 16], which includes a protein kinase substrate and the FLAG™ epitope to easily purify the proteins. All recombinant coding regions were amplified by PCR technique, digested and transferred to the eukaryotic expression vector pBNSEN [Pallisgaard, 1994] digested with NcoI and Klenow-treated Eco-RI. FIG. 1 shows the scheme of the various constructs. Proteins were expressed by transient transfection of the plasmids in COS cells, collection of the supernatants and purification on anti-FLAG antibody column (Sigma Aldrich Chem. Co.) or anti-uPAR antibody columns. Purified proteins gave single bands of the expected molecular weight in SDS-PAGE (not shown).

1b. Results

A mixture of three synthetic peptides (AVTYSRSRYLEC [SEQ ID NO: 9], YSRSRYLEC [SEQ ID NO: 14], SRYLEC [SEQ ID NO: 15]) derived from the linker region between D1 and D2 of uPAR, conjugated to Keyhole limpet hemocyanin (KLH) was used as immunogen in mice to generate monoclonal antibodies (see Methods).

b1. Identification of Positive Clones

In order to identify antibodies that would specifically recognize sequences within the AVTYSRSRYLEC [SEQ ID NO: 9] sequence of uPAR, we prepared three different soluble, recombinant, truncated suPAR proteins containing in part or in full this sequence (D2D3$_{84-274}$, D2D3$_{88-274}$, D2D3$_{93-274}$); in addition we also prepared recombinant soluble full-length suPAR (D1D2D1$_{1-277}$). Supernatants of hybridomas clones were screened in ELISA by coating plates with one of the four different soluble, recombinant, truncated suPAR proteins, incubating the plates with the hybridomas supernatants and then staining with an anti-mouse HRP-conjugated antibody (see Methods). The employed proteins, analyzed by SDS-PAGE and silver staining after reduction, were judged more than 95% (data not shown). Overall, three immunizations and 12 fusions were performed. 9850 clones were analyzed, of which 216 were found to be positive in an initial screening against the peptides themselves. Of these, 103 were confirmed positive in a re-testing. Of the 103 isolated and re-confirmed clones, a total of 11 were found to have the desired specificity (called 13E11, 14C4, 13A6, 1C5, 2A8, 4E11, 5F7, 7G1, 7G9, 8D3 and 8E3). They were highly positive for D2D3$_{84-274}$ but not for D2D3$_{93-274}$ and weakly positive for D1D2D3$_{1-277}$ and D2D3$_{88-277}$ (Table 1). The first three clones produced antibodies of the IgM isotype, while the other eight clones produced antibodies of the IgG1 isotype.

TABLE 1

| Clone | Subclass | ELISA | | | |
|---|---|---|---|---|---|
| | | D2D3 84 | D2D3 88 | D2D3 93 | D1D2D3 |
| 13E11 | IgM | ++++ | ± | – | ± |
| 13A6 | IgM | +++ | – | – | – |
| 14C4 | IgM | ++++ | + | – | + |
| 1C5 | IgG1 | ++ | ± | – | – |
| 2A8 | IgG1 | ++ | + | – | – |
| 4E11 | IgG1 | ++ | + | – | – |
| 5F7 | IgG1 | ++ | + | – | – |
| 7G1 | IgG1 | +++ | ++ | – | – |
| 7G9 | IgG1 | ++ | + | – | – |
| 8D3 | IgG1 | ++ | + | – | – |
| 8E3 | IgG1 | ++ | + | – | – |

EXAMPLE 2

General Characterization of Anti-Chemotactic Peptide Monoclonal Antibodies

2a. Materials and Methods
a1. Cell Transfection and Purification of Recombinant Soluble uPAR Molecules Semi-confluent COS7 cells were harvested in phosphate-buffered saline (PBS)-1 mM EDTA, washed with RPMI medium and the suspension (0.8 ml, 1-2×10$^7$ cells/ml in RPMI) electroporated in 0.4 cm Bio-Rad. cuvettes containing plasmid DNA (30 µg, 1 mg/ml in water) at 960 µF, 240V (GenePulser, Bio-Rad). After recovery overnight, cells were washed with PBS and supplemented with 50 ml of serum-free medium (D-MEM containing 1% Nutridoma NS). Every 4-5 days, conditioned medium was collected and fresh medium added. Recombinant proteins D2D3$_{93-274}$ and D2D3$_{93-274}$ were purified from the conditioned medium by passage over an anti-FLAG™ affinity column (M2 Affinity gel, Sigma) and eluted with 0.1 M glycine pH 3.0.

D1D2D3$_{1-277}$ was purified by a-uPAR antbody-column (mouse E4 Mab) [Bohuslav, 1995]. Purified D2D3$_{88-277}$ was prepared by cleavage of D1D2D3$_{1-277}$ with chymotrypsin followed by passage over the anti-uPAR affinity column [Bohuslav, 1995].

a2. Construction of Plasmids Expressing Truncated Cell Surface uPAR Molecules uPAR cDNA (nucleotide 311018) [Roldan, 1990] was cloned in the EcoRI site of pBSK-DNA, and the resulting plasmid was named uPAR-cDNA. GPI-D2D3$_{84-274}$ or GPI-D2D3$_{93-274}$ DNA were generated by PCR amplification of two different regions of uPAR-cDNA. The resulting plasmids were transferred (XhoI-NotI) into the Pn1-EGFP expression vector (Clontech) [Andolfo, 2002]. A scheme of the two constructs is presented in FIG. 1 along with the wild type uPAR. FIG. 1 also shows the relevant peptide sequences present in each construct.

a3. Cell Transfection with Plasmids Expressing Truncated Cell Surface uPAR Molecules 5×105 HEK-293 cells, cultured overnight in 60 mm tissue culture dishes, were transfected with 2 µg of GPI-D2D3$_{84-274}$, GPI-D2D3$_{93-274}$, or control vector and 25 µl of Effectene reagent (Quiagen) for 16 h at 37° C. (5% CO2). Transfected cells were selected with Geneticin at 1.5 mg/ml; the resulting clones of each transfection were cultured in the presence of 0.8 mglml Geneticin.

a4. Immunoprecipitation

Protein G Sepharose (Amersham-Pharmacia), capable to bind mouse IgG, or Protein-L agarose beads (Sigma) capable to bind mouse IgM, were washed three times with PBS. Coupling with the antibodies (5 µg purified IgG/IgM for each sample) was for 1 hour at 4° C. under continuous mixing. The resin was then washed with PBS. HEK-293 D2D3$_{84-274}$ or D2D3$_{93-274}$ expressing cells and HEK-293 wild type as a negative control were extracted with immunopreeipitatibn buffer (150 mM NaCl, 10 mM Tris; pH 7, 21 mM-PMSF, 10 µg/ml Aprotinin, 1% Triton X-100, 0.5% Sodium deoxicolic acid, 0.1% SDS) and the cell extracts were incubated with the resins form hour at 4° C. under continuous mixing. The resins were washed three times with immunoprecipitation buffer (1 ml a time). Sample buffer 2× (containing 2% beta-mercapto-ethanol as a reducing agent) was added to the resins pellet which was boiled for 3 minutes. The supernatant was analyzed by electrophoresis on a 10% polyacrylamide gel in the presence of SDS. After separation by SDS-electrophoresis, samples were electrotransferred onto a nitrocellulose membrane, blocked for 2 hours with 3% nonfat dry milk and incubated over-night with 1 µg/ml of an anti-uPAR polyclonal antibody. Finally, washed filters were incubated with goat anti-rabbit immunoglobulins/HRP conjugate (Amersham-Pharmacia) and detected by ECL.

a5. Immuno Blotting

10 µg of crude lysates of HEK-293 cells expressing D2D3$_{84-274}$ or D2D3$_{93-274}$ and HEK-293 wild type as a negative control were loaded in 10% SDS-PAGE acrylamide gel under reducing conditions and transferred onto a nitrocellulose membrane. The membrane was blocked for 2 hours with 3% nonfat dry milk and probed with purified antibodies (1 µg/ml) in TBS/0.5% BSA or 1 µg/ml of anti-uPAR monoclonal antibody as a positive control. Finally, washed filters were incubated with goat anti-mouse immunoglobulins/HRP conjugate (Amersham-Pharmacia) and detected by ECL.

a6. Flow Cytometry

Flow cytometry was performed using HEK-293 D2D3$_{84-274}$ or D2D3$_{93-274}$ expressing cells and HEK-293 wild type as a negative control. Detached cells (3×106 cells/ml) were incubated 30 min with PBS/10% human serum on ice to saturate Fc receptors. After washing with PBS/1% FCS, 100 µl of cell suspension were resuspended in 200 µl of hybridomas conditioned medium and incubated for 30 min on ice. After 2 washes with PBS/1% FCS the samples were incubated with a 1:500 dilution of phycoerythrin (PE)-labeled goat anti-mouse IgM or Igk (Southern Biotechnology) secondary antibody for 30 min on ice in the dark. After washing, the cells were analyzed using a FACScan flow cytometer (Berton Dickinson). Light scatter and fluorescence channels were set at logarithmic gain.

Results b1. Immunoprecipitation Analysis

Figure 2:
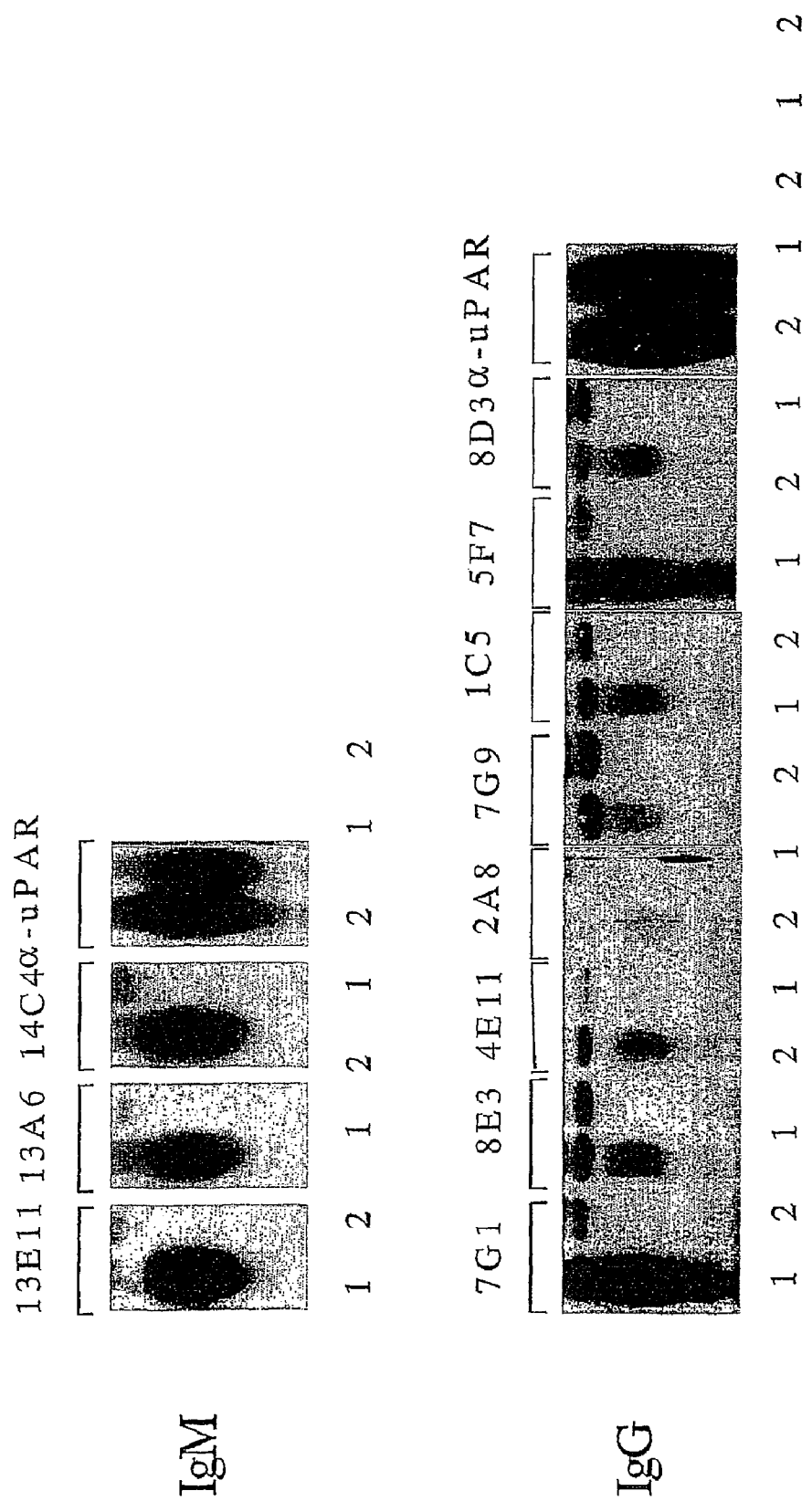

We tested the antibodies in immunoprecipitation using extracts from HEK-293 cells D2D3$_{84-274}$ and D2D3$_{93-274}$ expressing. As shown in FIG. 2, all clones recognized D2D3$_{84-274}$ only, but five antibodies (13E11, 14C4, 13A6, 5F7, 7G1) were highly positive in this assay.

Figure 3:
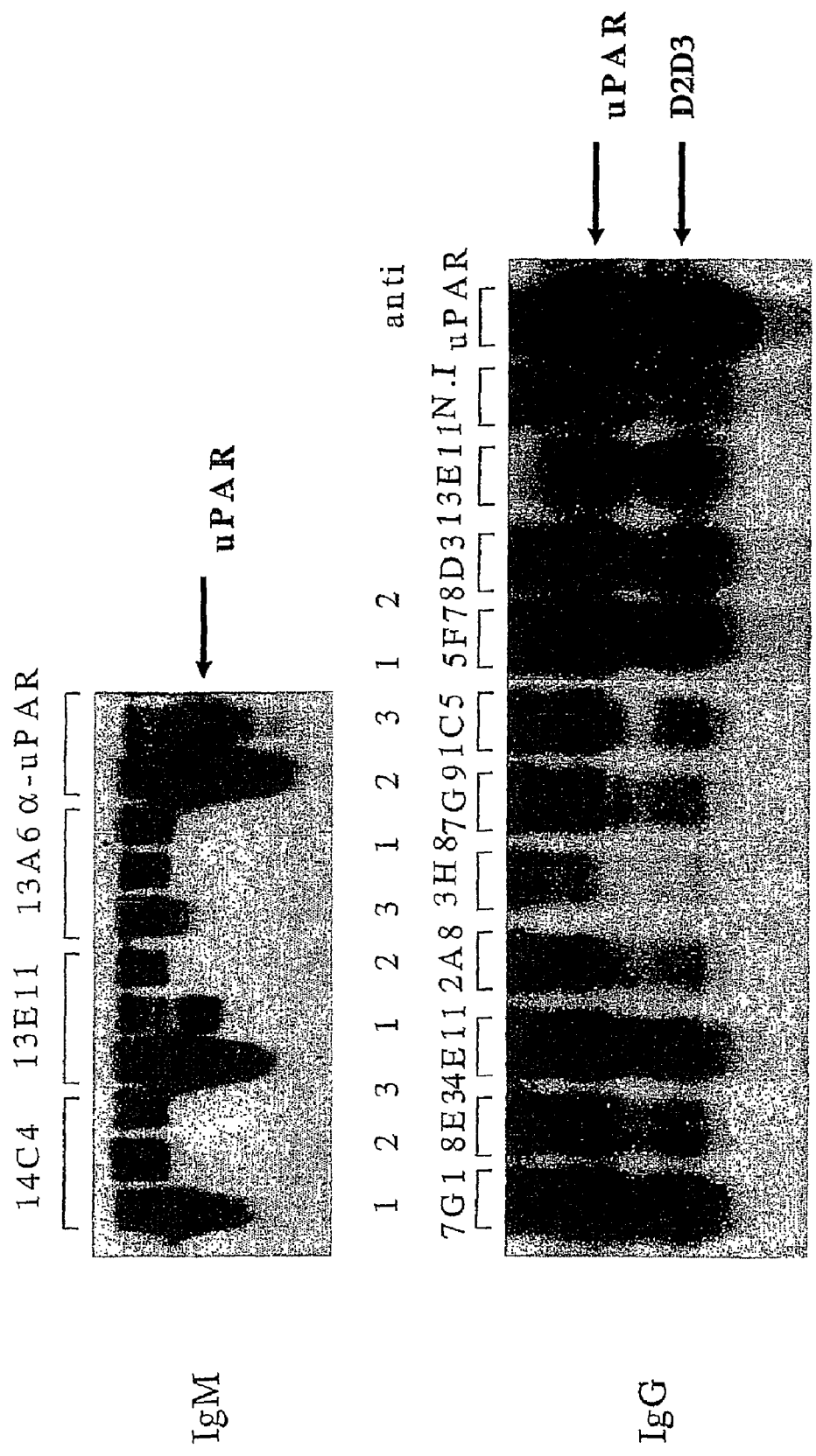
FIG. 3 shows the results of immunoprecipitation analysis on cell surface bound uPAR derivatives.
Upper panel: Immunoprecipitation using crude lysates of HEK-293 uPAR (1), LB6-uPAR (2) and HEK-293 (3)
Lower panel: Immunoprecipitation using crude lysates of HEK-293 uPAR expressing cells.

We also tested whether the antibodies would recognize cell surface bound uPAR derivatives by immunoprecipitating extracts of cells expressing full length GPI-linked D1D2D3 in both HEK-293 and LB6 cells. Since cell surface uPAR is endogenously cleaved between the D1 and D2 domain [Hoyer-Hansen, 1992] we expected two bands. As shown in FIG. 3, all immuno-precipitating antibodies equally recognized both the full-length as well as the cleaved bands of uPAR. These results show that the differential recognition by the antibodies of the cleaved vs. the full-length form is limited to the soluble proteins and not to the native proteins. Hence, unlike the soluble uPAR, in its native configuration the chemotactic epitope appears to be exposed to the antibody. In addition, the data show that cleaved uPAR on the cell surface contains the amino-terminal chemotactic epitope recognized by the antibody.

b2. Cytofluorometry

Figure 4:
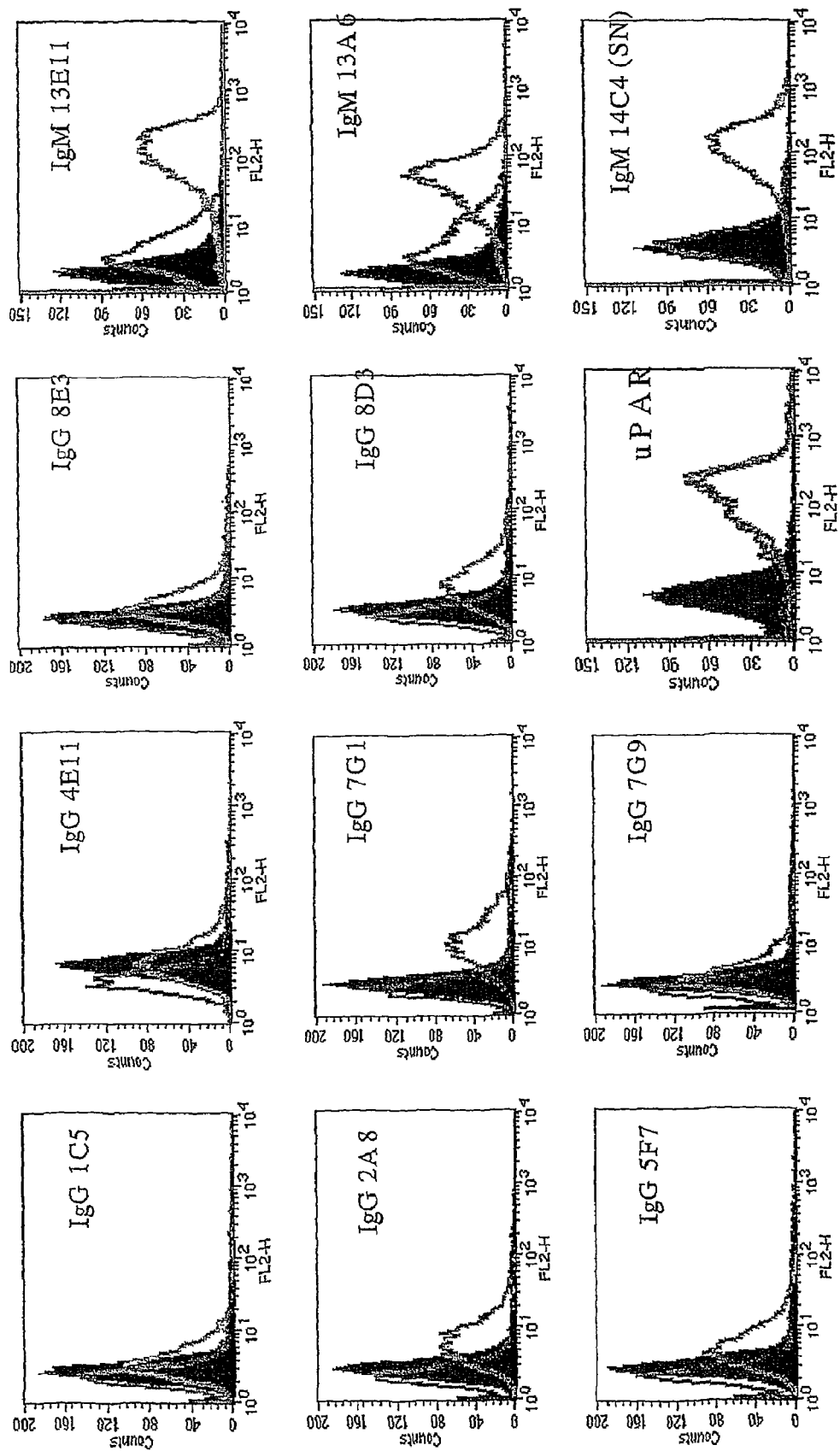
FIG. 4 shows the flow cytometric analysis of human HEK-293 $D2D3_{84-273}$ or $D2D3_{93-273}$ expressing cells and HEK-293 wild type with monoclonal antibodies and anti-uPAR antibody as a positive control. Filled black peak represents the HEK-293 wild type cells staining, gray peak the HEK-293 $D2D3 8427_3$ staining and black peak the HEK-293 $D2D3_{93-273}$ staining (SN . . . supernatant).

All antibodies were also tested in cytbfluorimetric analysis with HEK-293 expressing $D2D3_{84-274}$ or $D2D3_{93-274}$ and HEK-293 wild type as a negative control. As shown in FIG. 4, all clones gave a positive staining only with HEK-293 cells expressing $D2D3_{84-274}$ and not with HEK-293 expressing $D2D3_{93-274}$ or HEK-293 wild type, indicating that they recognize the chemotactic epitope (aa. 84-92). As a control, a polyclonal anti-uPAR antibody was used that recognized cells expressing both forms with the same intensity.

b3. Immunoblotting

We tested all antibodies in an immunoblotting assay using extracts from HEK-293 expressing $D2D3_{84-274}$ or $D2D3_{93-274}$ and HEK-293 wild type as a negative control. A weak positive signal was detected only with three clones 2A8, 7G1 and 5F7 (FIG. 5), suggesting that the reactivity of these antibodies is mostly dependent on a specific secondary structure, which is lost in the immunoblotting assay.

EXAMPLE 3

Development of an Immunofluorometric Assay to Quantitate the Levels of Cleaved suPAR in Human Body Fluids and Tissue Extracts 3a. Materials and Methods Immunofluorometric assay. For detection of soluble form of uPAR, immunoassay black plates (Maxisorp, Nunc) were coated for 16 h at 4° C. with 100 µl/well of anti-peptide monoclonal antibody (7G1) and anti-uPAR monoclonal antibody (R4) as a control (1 µg/ml, in 0.1 mol/l carbonate buffer, pH 9.5). Antibody R4 recognizes domain 3 of uPAR and therefore will identify any uPAR which is intact in that region. It has been used in myriads of assays and publications and was originally described in Ronne et al., FEBS Lett. 1991, 288, 233-236. The wells were rinsed three times with 300 µl/well of PBS containing 0.1% Tween 20. Wells were then treated for 30 min at 37 ∞ C with 100 µl/well 2% BSA in PBS. The wells were washed three times with 300 µl/well of PBS containing 0.1% Tween 20. The wells were then treated for 2 h at 37° C. with 100 µl/well of purified proteins ($D1D2D3_{1-277}$, $D2D3_{84-274}$, $D2D3_{88-277}$, $D2D3_{93-274}$) diluted in PBS/1% BSA. After three washes with PBS/0.1% Tween 20, the wells were then incubated for 1 h at 37° C. with 100 µl/well of anti-uPAR polyclonal antibody (M2 antiserum for 7G1 monoclonal, and SI369 for R4 monoclonal coating, 1 µg/ml in PBS/1% BSA. After three washes with PBS/0.1% Tween 20, the wells were then incubated for 1 h at 37° C. with 100 µl/well of goat anti-rabbit immunoglobulins/HRP conjugate (Amersham-Pharmacia). After three washes with PBS/0.1% Tween 20, 100 µl of freshly made Amplex Red (Molecular Probes) substrate solution (5 µM Amplex Red in 0.05M sodium phosphate, pH 7.4 with the addition of 10 µl H2O2 10 vol.) were added; after 1 hour at room temperature, protected from light, the HRP activity was detected fluorometrically using a fluorescence microplate reader (Victor3, Perkin Emler) set for excitation in the range of 530-560 nm and emission detection at 590 nm. Each sample was corrected for background fluorescence by subtracting the values derived from the negative control.

3b. Results b1. Identification of Suitable Monoclonals for ELISA or Immunofluorimetry In order to find the most suitable antibody for catching $D2D3_{84-274}$ in biological fluids or in selected human tissue extracts, we used two different version of an ELISA-type immunofluorometric assay. Among the two assay configurations (a) coating with monoclonal mouse antibody and detection with polyclonal anti-uPAR rabbit detection antibody and, b) coating with polyclonal anti-uPAR rabbit antibody and detection with mouse monoclonal antibody), the first showed to be the most sensitive configuration. From these experiments we found that 7G1 and 8D3 gave the highest signal to background ratio.

b2. Sensitivity and Linearity

A curve for the $D2D3_{84-274}$ immunofluorometric assay is shown in FIG. 6. There was a linear relationship (r=0.998) between the signal and the antigen concentration over the range from 0.125 ng/ml (39 nM) to 4 ng/ml (125 nM) The O.D.-range for the standard curve was 150000-2500000 (Arbitrary units). The data of FIG. 6 were obtained with the mouse monoclonal (7G1)/rabbit polyclonal (M2) immunoassay configuration. Limit of detection (LOD) The minimum detectable dose of the antigen ($D2D3_{84-274}$) was 0.125 ng/ml (2× background). Limit of quantitation (LOQ). The limit was 40× background b3. Specificity To test the specificity of the antibodies with respect to recombinant $D2D3_{84-274}$ versus recombinant $D1D2D3_{1-277}$, $D2D3_{88-277}$ and $D2D3_{84-274}$, we performed two different ELISA assays. First, we employed the standard ELISA method (spectrophotometric), coating immunoplates with the same amount of recombinant proteins ($D1D2D3_{1-277}$, $D2D3_{84-274}$, $D2D3_{88-277}$, $D2D3_{93-274}$) and using either R4 (that recognizes all forms of purified proteins) [Ronne, 1994] or 7G1 (see above) as detecting antibodies. As shown in FIG. 7A, while R4 monoclonal antibody generated overlapping concentration profiles with the four purified proteins, 7G1 monoclonal antibody recognized $D2D3_{84-274}$ with a specificity 3-4 fold higher than $D2D3_{88-274}$ and at least 100 fold higher than $D2D3_{93-274}$. In addition, it also recognized $D1D2D3_{1-277}$, and $D2D3_{88-277}$ but 3-4 fold less than $D2D3_{84-274}$. In a second assay, we employed the immunofluorimetric assay (FIG. 7B). With this assay, $D2D3_{84-274}$ was the only form detectable at concentrations up to 30 ng/ml, while only $D1D2D3_{1-277}$ was weakly detectable at the higher concentration used (30 ng/ml). R4 antibody recognized equally well all proteins, as expected. No signal above background level was observed when an irrelevant monoclonal antibody of the same subclass as 7G1 (IgG1), MOPC, was used as the catching antibody, demonstrating detection specificity (not shown).

Linearity and Recovery. Three urine samples used in the linearity study wer diluted ten-, twenty-, forty- and eighty-fold. For each sample, the dilution curve was close to linear, confirming the parallelism between the calibrator and urine samples (FIG. 8A).

Specific signal recovery was determined by addition of increasing concentrations of purified $D2D3_{84-274}$ (4, 2, 1, 0.5 µg/L) to a fixed 1:10 dilution of three different urine samples. In all samples, the recovery of the internal standard was between 94% and 105% for sample 1, 97% and 104% for sample 2 and 95% and 105% for sample 3 (FIG. 8B).

Precision. The intra-assay coefficient of variation of the ELISA was 10% as determined by assaying 20 independent 1/10 dilutions of a urine samples pool derived from seven colon cancer patients on the same ELISA plate. The interassay coefficient of variation was 15.2% as determined by analyzing the same dilution of a urine samples pool derived from seven colon cancer patients on 8 separate days.

Accuracy. Two-fold serial dilutions of one urine sample showed a dose response in the ELISA that was linear up to a dilution of 1/10. The regression coefficient was calculated to be 0.999. The recovery was tested by the addition of 0.6 ng/ml of purified $D2D3_{84-274}$ to the same dilution series of the urine sample (not shown). The recovery of the internal standard was 101% as determined from the slopes of the regression lines (not shown).

Robustness. We examined the stabilities of the different suPAR forms after repeating freezing and thawing (6-7 cycles) of a urine samples pool derived from seven colon cancer patients. We observed no significant changes in absolute concentration of the suPAR forms.

EXAMPLE 4

Determination of the Presence and Concentration of Cleaved suPAR Fragments in Serum and Urine of Cancer Patients 4a. Materials and Methods
a1. Materials We have used urines and serum samples from 82 cancer patients and 40 controls. Fasting morning urine samples were collected and stored at −80° C. For the assays the samples were diluted 1:10 in PBS/1% BSA:
a2. Immunofluorimetric Assay The immunofluorimetric assay is described in the Methods section of Example III. MOPC is an irrelevant mouse IgG antibody used as a control.
Results In order to test whether the above described assay would be able to measure the concentrations of cleaved suPAR in human body fluids, a pilot study was carried out in which suPAR concentrations were measured in urine or serum samples from a total of 115 patients (40 healthy volunteers, and 75 patients with different malignant carcinomas). The study was divided in two groups. The data are summarized in Table 2, in which the first two rows represent the first group of patients, and the third and fourth row the second group of patients. Overall, patients with tumors had a clearly higher level of both total and cleaved suPAR (D2D3) in their urine with respect to the control patients. The effect was in general lower in the serum. Interestingly, there appears to be a trend in which the "cleaved suPAR (D2D3) measurement showed a clearer difference than the measurement of total suPAR.

TABLE 2

Measurement of D2D3 levels in urine and serum of normal and tumor-patients

| | | Total suPAR (R4)* | | D23 (7G1)* | |
|---|---|---|---|---|---|
| Samples | n ° | Mean (SD) | Median | Mean (SD) | Median |
| controls (urine) | 30 | 0.76 (1.25) | 0.29 | 0.72 (0.74) | 0.485 |
| tumors (urine) | 53 | 3.18 (3.76) | 2.19 | 3.97 (5.67) | 1.7 |
| controls (serum) | 10 | 2.12 (1.43) | 2.31 | 2.41 (1.57) | 2.11 |
| tumors (serum) | 22 | 3.36 (2.75) | 2.76 | 4.97 (3.51) | 4.17 |

The study was conducted in two groups. Rows 1 and 2 refer the data in the first group of sample, rows 3 and 4 refer to a second group of collected samples.
*The data are expressed in ng/ml.

We conclude that the present immunofluorimetric assay is well suited to measure the level of D2D3 in the serum and urine of both normal individuals and tumor patients, and by extension also in patients of other diseases. Moreover, preliminary studies suggest that while in certain types of tumors (i.e. colon) the two parameters, total suPAR and D2D3, are directly correlated, and hence give similar types of information, in other types of tumors (prostate) they are not. In this case, the measurement of D2D3 would give additional and novel information, different from the measurement of total suPAR.

EXAMPLE 5

Effect of Monoclonal Antibodies Recognizing the Chemotactic Epitope of uPAR on Cell Migration Table 3 summarizes the results obtained in a series of preliminary experiments carried out to test whether the monoclonal antibodies produced against the chemotactic region of uPAR can block the migration of cells.

TABLE 3

Effect of antibodies to the uPAR chemotactic epitope on monocytes cell migration

| Additions | % basal migration | % induced migration (ATF) | Migration fold increase | % of inhibition |
|---|---|---|---|---|
| none | 100 ± 9 | 339 ± 29 | 3.4 | — |
| MOPC | 110 ± 7 | 299 ± 24 | 2.72 | — |
| 7G1 | 86 ± 10 | 210 ± 27 | 2.44 | 10 |
| 1C5 | 79 ± 9 | 244 ± 9 | 3.01 | — |
| 8E3. | 106 ± 13 | 282 ± 18 | 2.66 | 2 |
| 5F7 | 63 ± 11 | 214 ± 25 | 3.39 | — |
| 7G9 | 139 ± 7 | 336 ± 20 | 2.42 | 17 |
| 4E11. | 170 ± 40 | 341 ± 29 | 2 | 31 |
| 8D3 | 110 ± 14 | 195 ± 9 | 1.77 | 39 |
| 2A8 | 205 ± 33 | 338 ± 32 | 1.65 | 43 |
| MOPC | 120 ± 12 | 349 ± 28 | 2.91 | — |
| Rabbit IgG | 103 ± 16 | 303 ± 15* | 2.94 | — |
| N-77 (anti-FPRL1) | 67 ± 7 | 82 ± 8* | 1.2 | 78 |

Antibodies concentration: 50 μg/ml
Results represent the average of 4 experiments in triplicate
The percentage of inhibition is referred to MOPC treatment
*MMK-1 was used as chemoattractant Cells: we used freshly isolated monocytes, because these cells are in general most responsive to D2D3. As a positive control we have tested that these cells respond to the FPRL1 ligand 1.0 mM MMK-1 by 300%, and their response is inhibited by the specific anti-FPRL1 antibody (already adjusted at its best concentration) by 78%.

Stimulus: we used ATF, the N-terminal fragment of uPA. The rationale for this choice is that in order to screen for the best antibodies, we have chosen first the most difficult stimulus, i.e. the uPA derived fragment which cannot ID cleave UPAR and, hence, produce D2D3. Therefore the effect of the antibodies should be on the cell-surface uPAR which changes conformation upon binding of ATF. Since the antibodies were raised against the chemotactic peptide contained in D2D3 of uPAR, and since many of the antibodies immunoprecipitate D2D3, with all likelihood most of the antibodies would have had an effect on D2D3-dependent migration.
Results We have tested whether the antibody is able to affect the basal (i.e. non stimulated) migration. As seen in the Table 3, Mabs 7G9, 4E11 and 2A8 do in particular increase basal migration.

In the absence of antibodies, ATF induced a 339% (i.e. 3.39 fold) increase in chemotaxis of monocytes. All the antibodies (even the non specific) had some inhibitory effect. Therefore we consider the average value of the MOPC antibody as the assay control. Under these conditions, the antibody 8D3 has a good inhibitory activity (40%), which can be reconfirmed at lower concentration. Also 4E11 and 5F7 are promising. Two more (2A8 and 4E11) appear to inhibit chemotaxis even though they increase basal migration. The antibodies scoring positive in the assay are therefore expected to inhibit all migration in cancer and hence invasion and metastasis, as long as, and for the part of, that is dependent upon uPAR.

EXAMPLE 6

Effects of Monoclonal Antibodies Recognizing the Chemotactic Epitope of uPAR on Chemotaxis of Monocytes and Tumor Proliferation 6a. Materials and Methods
a1) Cell Culture Tumor cell lines A431, HT-1080, Hela, PC-3, HT29, A549 and A2058 were grown in Dulbecco's modified Eagle's medium (Invitrogen) supplemented with 10% fetal calf serum. Transfected cells were grown in Dulbecco's modified Eagle's medium (Invitrogen) supplemented with 10% fetal calf serum. Transfected cells medium also contained the antibiotic G418 (0.8 mg/ml).

a2) Cell Transfection and Purification of Recombinant Soluble uPAR Molecules

Semi-confluent COS7 cells were harvested in phosphate-buffered saline (PBS)-1 mM EDTA, washed with RPMI medium and the suspension (0.8 ml, $1-2 \times 10^7$ cells/ml in RPMI) electroporated in 0.4 cm Bio-Rad cuvettes containing plasmid DNA (30 µg, 1 mg/ml in water) at 960 µF, 240 V (GenePulser, Bio-Rad). After recovery overnight, cells were washed with PBS and supplemented with 50 ml of serum-free medium (D-MEM containing 1% Nutridoma NS). Every 4-5 days, conditioned medium was collected and fresh medium added. Recombinant proteins $D2D3_{84-274}$ and $D2D3_{93-274}$ were purified from the conditioned medium by passage over an anti-FLAG™ affinity column (M2 Affinity gel, Sigma) and eluted with 0.1 M glycine pH 3.0.

a3) Cell Transfection with Plasmids Expressing FPRL1

$5 \times 10^5$ HT1080, A2058 and A549 cells, cultured overnight in 60 mm tissue culture dishes, were transfected with 1 µg of FPRL1-expression vector and 25 µl of Effectene reagent (Quiagen) for 16 h at 37° C. (5% CO2).

Transfected cells were selected by Geneticin at 1.5 mg/ml; the resulting clones of each transfection were cultured in the presence of 0.8 mg/ml Geneticin.

a4) Tumor Cell Lines Transfection with FPRL1

In order to test for the chemotactic response different tumor cell lines (HT1080, A2058, A549) were transfected with FPRL1-expression vector. The morphology and the cell growth of transfected and untransfected cells were similar, meaning that FPRL1 expression did not alter the properties of the cells.

a5) Proliferation Assay

Different tumor cell lines were seeded at 5000-10000 cells/well into 12-well plates in complete medium (DMEM+10% FBS) and were allowed to adhere for 24 hours before the procedure. Then different concentrations of antibodies (MOPC and 8D3) were added to the cells and left for several days in the same medium. After 5 or 7 days, cells were disloged by trypsinization and counted in a Coulter Counter (Coulter Electronics LTD). All of the samples were prepared in duplicate.

a6) Growth in Soft Agar

Cells ($4-8 \times 10^3$ cells/well) were suspended in in 2 ml of 0.3% Noble agar (Difco) supplemented with complete medium (DMEM+10% FBS) in which were added different concentrations of antibodies (MOPC and 8D3). The suspension was layered over 2 ml of 0.6% agar-medium base layer in 6-multiwell cluster dishes, After 14 days, the cells were stained with nitro blue tetrazolium (Sigma Chemical Co.).

a7) Chemotaxis Assay

Migration of freshly isolated human monocytes was assessed by a 48-well microchemotaxis chamber (Neuro Probe, Cabin John, Md.). Twenty-six µl of chemoattractants at different concentrations in medium (serum-free RPMI-1640) was placed in the wells of the lower compartment of the chamber, and 50 µl cell suspension ($10^6$ cell/ml) were added to the upper compartment. The two compartments were separated by an uncoated filter of either a 5 µm pore size polycarbonate filter (Neuro Probe). After 90 minutes incubation at 37° C. in humidified air with 5% $CO_2$ the filter was removed, scraped, fixed and stained with Diff-Quick (Dade Diagnostics). The number of migrated cells in eight high-powered fields was counted by light microscopy. Results are expressed as the mean (±SD) value of the migration in triplicate samples and are representative of at least three experiments performed. Migration in the absence of chemoattractant is considered 100%. The cells were pre-incubated with the antibodies tested as inhibitors of migration for 20 min at 37° C. in humidified air with 5% $CO_2$.

a8) Invasion Assay

In vitro tumor cell invasion was assessed using a Biocoat Matrigel invasion chamber (BD Biosciences) with cell culture inserts containing an 8 µm pore size membrane with a thin Matrigel basement membrane matrix. One-half milliliter of cells ($5 \times 10^4$ cells/ml) in serum free DMEM was added to the cell culture insert of a Biocoat Matrigel invasion chamber. Different concentrations of D2D3 were added in the outer chamber as a chemoattractant. The cells were then incubated at 37° C. in humidified 5% CO2 conditions for 24 h. To quantitate tumor cell invasion, noninvading cells were removed from the top surface of the membrane by scrubbing gently with a cotton-tipped swab. The cells on the bottom surface of the membrane were fixed with Diff-Quik stain set (Dade Behring) and counted to determine the number of cells that passed through the Matrigel and membrane layers.

a9) Tumor Xenograft Models

Female nu/nu mice, aged 4 to 5 weeks, were fed ad libitum water and an irradiated standard rodent diet. Mice were housed in static microisolators on a 12 hours light cycle at 22° C. and 40% to 60% humidity. Tumors were established by subcutaneously injection of human A2058 melanoma cells ($5 \times 10^6$ cells in 100 µl PBS), A549 lung cancer cells ($3 \times 10^6$ cells in 100 µl PBS) and HT1080 fibrosarcoma cells ($2 \times 10^6$ cells in 100 µl PBS). Estimated tumor weight was calculated using the following formula: tumor weight (in milligrams)=$(w^2 \times l)/2$, where w=width and l=length in millimeters. Tumor measurements continued until all animals in each group reached the endpoint. The endpoint was the maximum tumor size permitted for each model (1000 mg). Tumors were measured three times weekly.

6b) Results
b1) Effect of Antibodies on uPAR-Dependent Chemotaxis

Chemotaxis experiments were performed using freshly isolated monocytes in response to D2D3 in the presence of Mab 8D3 plus the unspecific antibody MOPC as a control at 5 µg/ml final concentration (FIG. 9). Concentration dependent analysis on the effect of Mab 8D3 in chemotaxis experiments was additionally performed using monocytes in response to ATF.

FIG. 10 depicts that by using three different concentrations of Mab 8D3 (50, 10, 1 µg/ml) plus the unspecific Mab MOPC as a control, about 50-70% of inhibition at all three concentrations is obtained.

b2) Effect of Antibodies on Tumor Cell Lines Proliferation Initial Screening

Seven tumor cell lines were used: HT-29 (colon carcinoma), A549 (lung carcinoma), HT-1080 (fibrosarcoma), PC-3 (prostate carcinoma), Hela (ovarian carcinoma), A431 (epidermoid carcinoma) and A2058 (melanoma), and characterized for the presence of uPAR in immunoprecipitation assays on biotinylated extracts after deglycosylation, using an antibody recognizing uPAR (R2). As shown in FIG. 11, all cell lines tested expressed uPAR. Untransfected HEK-293 cells served as a negative control.

Proliferation Assay

The seven tumor cell lines were treated with Mabs 8D3 in the proliferation assay, to test the anti-proliferative activity. Mab 8D3 was able to inhibit cell growth in all cell lines tested with a different efficacy (FIG. 12A).

The concentration-dependence of the anti-proliferative activity of Mab 8D3 was tested using three different concentrations (10, 1 and 0.1 µg/ml.) Highest activity was found at 10 µg/ml (FIG. 12B).

The effect of Mab 8D3 treatment was evaluated in soft agar growth-assay using HT1080 cells (transfected with FPRL1 and untransfected as a control). Colony formation was analysed after treatment with Mabs MOPC and 8D3 at 50 µg/ml comparing the HT1080 untransfected cells versus transfected. As shown in FIG. 13, 8D3 treatment caused a dramatic inhibition of colony formation in both cell lines.

b3) In Vivo Tumor Model

Mice were inoculated subcutaneously with the selected cells (selected for their response to D2D3 in chemotaxis experiments and for their response to the 8D3 antibody in proliferation experiments using HT1080, A2058 and A549) and the growth of the tumor was followed by conventional methods. Initially six mice were inoculated for each cell line tested using a different number of cells ($5 \times 10^6$/mouse for A2058, $3 \times 10^6$/mouse for A549 and $2 \times 10^6$/mouse for HT1080). The tumors were measured 5 days after injection. The mice treated with HT1080 were sacrified 14 days after inoculation. Three groups of mice were tested (10-12 animals/group for HT1080 cells and 6 animals/group for A2058) untreated or treated with the Mabs MOPC and 8D3. The mice were inoculated with a cell suspension containing or devoid of Mabs at 200 µg/mouse final concentration or alternatively Mabs were administered i.p. once a week for 2-3 weeks (see legends of figures for details).

Table 4 shows the results obtained with HT1080-FPRL1. In all three experiments the mice treated with Mab 8D3 showed a dramatic decrease of tumor formation with respect to untreated or MOPC-treated mice

TABLE 4

Effect of Mab 8D3 on HT1080-FPRL1 xenograft mice

| Treatments | 1st Experiment | | 2nd Experiment | | 3rd Experiment | |
|---|---|---|---|---|---|---|
| | Tumors grown | No tumors | Tumors grown | No tumors | Tumors grown | No tumors |
| No antibody | 6 | 6 | 7 | 3 | Not tested | Not tested |
| MOPC (200 µg/mouse) | 3 | 9 | 7 | 3 | 7 | 3 |
| 8D3 (200 µg/mouse) | 1 | 11 | 4 | 5 | 1 | 9 |

Female nu/nu mice were injected s.c. with $1.5 \times 10^6$ cells/each. Five days after injections the tumors are measured every 2-3 days. 4 and 11 days after cell injection, Mabs or PBS were injected i.p. (200 µg/mouse). The mice were sacrified after 19 days.

REFERENCES

Aguirre Ghiso, J. A., Kovalski, K. and Ossowski, L. (1999). "Tumor dormancy induced by downregukation of urokinase receptor in human carcinoma involves integrin and MAPK signalg." *J. Cell Biol.* 147(1): 89-104.

Andolfo, A., English, W., Murphy, G., Blasi, F. and Sidenius, N. (2002). "Metalloproteolytic cleavage of the urokinase-type plasminogen activator receptor leads to exposure of epitopes not present in the intact soluble receptor." *Thromb. Haemost.* 88: 298-306.

Beaufort, N., Leduc D, Rousselle J C, Magdolen V, Luther T, Namane A, Chignard M, Pidard D. (2004). "Proteolytic regulation of the urokinase receptor/CD87 on monocytic cells by neutrophil elastase and cathepsin G." *J. Immunol.* 172: 540-549.

Behrendt, N., Ploug, M., Patthy, L., Houen, G., Blasi, F. & Dane, K. (1991). "The ligand-binding domain of the cell surface receptor for urokinase-type plasminogen activator." *J. Biol. Chem.* 266: 7842-7847.

Blasi, F. a. C., P. (2002). "uPAR: a versatile signaling orchestrator." *Nature Rev. Mol. Cell Biol.* 3: 932-943.

Blasi, F (1997). uPAR-uPA-PAI-1: a key intersection in proteolysis, adhesion and chemotaxis. Immunol. Today, 18, 415-417.

Bohuslav J, Horejsi V, Hansmann C, Stockl J, Weidle U H, Majdic O, Bartke I, Knapp W, Stockinger H. (1995). Urokinase plasminogen activator receptor, beta 2-integrins, and Src-kinases within a single receptor complex of human monocytes. J Exp Med. 181:1381-90.

Braat E A, Jie A F, Ronday H K, Beekman B, Rijken D C. (2000). Urokinase-mediated fibrinolysis in the synovial fluid of rheumatoid arthritis patients may be affected by the inactivation of single chain urokinase type plasminogen activator by thrombin. Ann Rheurm Dis.;59(4):315-8.

Cerinic M M, Generni S, Partsch G, Pignone A, Dini G, Konttinen Y T, Del Rosso M. (1998). Synoviocytes from osteoarthritis and rheumatoid arthritis produce plasminogen activators and plasminogen activator inhibitor-1 and display u-PA receptors on their surface. Life Sci.; 63):441-53

Chapman, H. A. (1997). "Plasminogen activators, integrins, and the coordinated regulation of cell adhesion and migration." *Curr. Opin. Cell Biol.* 9: 714-724.

Coleman, J. L., Gebbia J. A., Benach J. L. (2001). "*Borrelia burgdorferi* and other bacterial products induce expression and release of the urokinase receptor." *J. Immunol.* 166: 473-480.

Cunningham, O., Andolfo, A P, Santovito, A L, Blasi, F. and Sidenius, N. (2003). "Differential lipid raft partitioning of the urokinase receptor regulates its biological functions and is controlled by receptor dimnerization." *EMBO J.* 22: 5994-6003.

Degryse, B., Orlando, S., Resnati, M., Rabbani, S. A. and Blasi, F. (2001). "Urokinase/urokinase receptor and vitronectin/avb3 integrin induce chemnotaxis and cytoskeleton reorganization through different signaling pathways." *Oncogene* 20: 2032-2043.

Degryse, B., Resnati, M., Rabbani, S. A., Villa, A., Fazioli, F., & Blasi, F. (1999). "Src-dependence and pertussis-toxin sensitivity of urokinase receptor-dependent chemotaxis, and cytoskeleton reorganization in rat smooth muscle cells via the urokinase receptor." *Blood* 94: 649-662.

Fazioli, F., Resnati, M, Sidenius, N, Higashimoto, Y, Appella, E and Blasi, F. (1997). "The urokinase-sensitive region of the urokinase receptor is responsible for its potent chemotactic activity." *EMBO J.* 16: 7279-7286.

Florquin, S., Van der Berg, J G, Olszyna, D P, Claessen, N, Opal, S M, Weeining, J J and Van der Poll, T. (2001). "Release of urokinase plasminogen activator receptor during urosepsis and endotoxemia." *Kidney Int.* 59: 2054-2061.

Furlan, F., Orlando, S., Laudanna, C., Resnati, M., Basso, V., Blasi, F. and Mondino, A. (2004). "A soluble form of the urokinase receptor inhibits monocyte migration by preventing integrin-dependent cell adhesion." *J. Cell Sci.* 117: 2909-2916.

Hoyer-Hansen, G., Behrendt, N., Ploug, M., Dano, K. and Preissner, K. T. (1997). "The intact urokinase receptor is required for efficient vitronectin binding: receptor cleavage prevents ligand interaction." *FEBS Lett* 420(1): 79-85.

Hoyer-Hansen, G., Ploug, M., Behrendt, N., Ronne, E. and Dano, K. (1997). "Cell surface acceleration of urokinase-catalyzed receptor cleavage." *Eur J Biochem* 243: 21-26.

Hoyer-Hansen, G., Ronme, E., Solberg, H., Behrendt, N., Ploug, M., Lund, L. R., Ellis, V. and Dano, K. (1992). "Urokinase plasminogen activator cleaves its cell surface receptor releasing the ligand-binding domain." *J Biol Chem* 267: 18224-18229.

Koolwijk, P., Sier, C. F. M., Peters, E., Hanemaaijer, R., Sidenius, N., Blasi, F. and van Hinsbergh, V. W. M. (2001). "Proteolysis of the uPA receptor by endothelial cell-derived matrix metalloprotease(s). Implication for angiogenesis in 3-D fibrin matrices in vitro." *Blood* 97.: 3123-3131.

Masucci, M. T., Pedersen, N. and Blasi, F. (1991). "A soluble ligand-binding mutant form of the human urokinase plasminogen activator receptor." *J. Biol. Chem.* 266: 8655-8658.

Mizukami, I., Faulkner N E, Gyetko M R, Sitrin R G, Todd RF 3rd. (1995). "Enzyme-linked immunoabsorbent assay detection of a soluble form of urokinase plasminogen activator receptor in vivo." *Blood.* 86: 203-211.

Mustoki, S., Sidenius, N. Sier, C. F. M. Blasi, F. Elonen, E., Alitalo, R. and Vaheri, A. (2000). "Levels of soluble urokinase receptor correlate with number of circulating tumor cells in acute leukemia and decrease rapidly during chemotherapy." *Cancer. Res.* 60: 7126-7132.

Nguyen, D. H., Catling, A. D., Webb, D. J., Sankovic, M., Walker, L. A., Somlyo, A. V., Weber, M. J. and Gonias, S. L. (1999). "Myosin light chain kinase functions downstream of Ras/ERK to promote migration of urokinase-type plasminogen activator-stimulated cells in an integrin-selective manner." *J Cell Biol* 146(1): 149-64.

Nguyen, D. H., Webb, D. J., Catling, A. D., Song, Q., Dhakephalkar, A., Weber, M. J., Ravichandran, K. S. and Gonias, S. L. (2000). "Urokinase-type plasminogen activator stimulates the Ras/Extracellular signal-regulated kinase (ERK) signaling pathway and MCF-7 cell migration by a mechanism that requires focal adhesion kinase, Src, and Shc. Rapid dissociation of GRB2/Sps-Shc complex is associated with the transient phosphorylation of ERK in urokinase-treated cells." *J. Biol. Chem.* 275: 19382-19388.

Ossowski, L., Aguirre Ghiso, J. A. (2000). "Urokinase receptor and integrin partnership: coordination of signaling for cell adhesion, migration and growth." *Curr. Opin. Cell Biol.* 12: 613-620.

Pallisgaard, N., Pedersen, F S, Birkelund, S, Jorgensen, P. (1994). "Common multiple cloning sites in a set of vectors for expression of eukaryotic genes in mammalian, insect and bacterial cells." *Gene* 138: 115-118.

Pedersen, N., Schmitt, M., Ronne, E., Nicoletti, M. I. Hyer-Hansen, G., Conese, M., Giavazzi, R., Dan, K., Kuhn, W. Janicke, F. and Blasi, F. (1993). "An unoccupied, water soluble urokinase receptor is present in the ascitic fluid and plasma from patients with ovarian cancer." *J. Clin. Invest.* 92: 2160-2167.

Ploug, M. (2003). "Structure-Function Relationships in the interaction between the urokinase-type plasminogen activator and its receptor." *Curr. Pharmac. Design* 9: 1499-1528.

Ploug, M., Oestergard, S., Gardsvoll, H., Kovalski, K., Holst-Hansen, K., Hohm, A., Ossowski, L. and Danoe, K. (2001). "Peptide-derived antagonists of the urokinase receptor. Affinity maturation by combinatorial chemistry, identification of finctional epitopes, and inhibitory effect on cancer cell intravasation." *Biochemistry* 40: 12157-12168.

Preissner, K., Kanse, S. M. and May, A. E. (2000). "Urokinase receptor: a molecular organizer in cellular communication." *Curr. Opin. Cell Biol.* 12: 621-628.

Resnati, M., Guttinger, M., Valcamonica, S., Sidenius, N., Blasi, F. and Fazioli, F. (1996). "Proteolytic cleavage of the urokinase receptor substitutes for the agonist-induced chemotactic effect." *EMBO J.* 15: 1572-1582.

Resnati, M., Pallavicini, I., Wang, Y. M., Oppenheim, J., Serhan, C: N., Romano, M. and Blasi, F. (2002). "The fibrinolytic receptor for urokinase activates the G protein-coupled chemotactic receptor FPRL1/LXA4R." *Proc. Natl. Acad. Sci. U.S.A.* 99: 1359-1364.

Roldan, A. L, Cubellis, M. V., Masucci, M. T., Behrendt, N., Lund, L. R., Dan, K. and Blasi, F. (1990). "Cloning and expression of the receptor for human urokinase plasminogen activator, a central molecule in cell-surface plasmin dependent proteolysis." *EMBO J.* 9: 467-474.

Ronne, E., Behrendt, N, ploug, M, Nielsen, H J, Wollisch, E, Weidle, U, Dano, K and Hoyer-Hansen, G. (1994). "Quantitation of the receptor for urokinase plasminogen activator by enzyme-linked immunosorbent assay." *J. Immunol. Meth.* 167: 91-101.

Selleri, C., Montuori, N., Ricci, P., Visconte, V., Carriero, M V, Sidenius, N., Serio, B., Blasi, F., Rotoli, B., Rossi, G., Ragno, P. (2005) Involvement of the urokinase-type plasminogen activator receptor in hematopoietic stem cell Blood. In press Sidenius, N., Olsen, J. E., Sier, C. F. M. Blasi, F., Ullum, H. (2000). "Increased plasma levels of soluble urokinase receptor in HIV infected patients are highly correlated with survival." *Blood* 96: 4091-4095.

Sidenius, N., Sier, C F. M. and Blasi, F. (2000). "Shedding and cleavage of the urokinase receptor (uPAR): Identification and characterisation of uPAR fragments in vitro and in vivo." *FEBS L.* 475: 52-56.

Sier, C., Nicoletti, I., Santovito, M. L., Frandsen, T., Aletti, G., Ferrari, A., Lissoni, A., Giavazzi, R. Blasi, F. and Sidenius, N. (2004). "Metabolism of tumour-derived urokinase receptor and receptor fragments in cancer patients and xenografted mice." *Thrombosis and Haemostasis* 91: 403-411.

Sier, C., Stephens, R, Bizik, J, Mariani, A, Bassan, M, Pedersen, N, Frigerio, L, Ferran-, A, Dan, K, Brünner, N and Blasi, F. (1998). "Full-size, GPI-anchor free urokinase receptor is increased in serum of ovarian cancer patients." *Cancer Res.* 58: 1843-1849.

Sier, CFM, Sidenius, N, Mariani, A, Aletti, A., Agape, V., Ferrari, A.,

Stephens, R., Brunner, N., Blasi, F. (1999) Presence of soluble urokinase-type plasminogen activator receptor in urine and possible clinical relevance. Lab. Invest. 79, 717-722.

Simon, D. I., Wei, Y., Zhang, L., Rao, N. K., Xu, H., Chen, Z., Liu, Q., Rosenberg, S., Chapman, H. A. (2000). "Identification of a urokinase receptor-integrin interaction site. Promiscuous regulator of integrin function." *J. Biol. Chem.* 275: 10228-10234.

Slot, O., Brunner, N., Locht, H., Oxhøhm, P. and Stephens, R. W. (1999). Soluble urokinase plasminogen activator receptor in plasma of patients with inflammatory rheumatic disorders: increased concentrations in rheumatoid arthritis. Ann. Rheum. Dis. 58, 488-492.

Stephens, R. W., Nielsen, H. J., Christensen, I. J., Thorlacius-Ussing, O., Sorensen, S., Dano, K, Brunner, N. (1999). "Plasma urokinase receptor levels in patients with colorectal cancer: relationship to prognosis." *J. Natl Cancer Inst* 91: 869-874.

Stoppelli, M. P., Corti, A., Soffientini, A., Cassani, G., Blasi, F. and Assoian, R. K. (1985). "Differentiation-enhanced binding of the amino-terminal fragment of human urokinase plasminogen activator to a specific receptor on U937 monocytes." *Proc. Natl. Acad. Sci. USA* 82: 4939-4943.

Vassalli, J.-D., Baccino, D. and Belin, D. (1985). "A cellular binding site for the Mr 55,000 form of the human plasminogen activator urokinase." *J. Cell Biol.* 100: 86-92.

Wei, Y., Eble, J. A., Wang, Z., Kreidberg, J. A. and Chapman, H. A. (2001). "Urokinase receptor promotes b1 integrin function through interactions with integrin a5b1." *Mol. Biol. Cell* 12: 2975-2986.

---

The invention claimed is:

1. A monoclonal antibody or a fragment thereof specific for the chemotactic epitope of activated urokinase-type plasminogen activator receptor (uPAR), wherein the monoclonal antibody is selected from the group consisting of 7G1 and 8D3.

2. The monoclonal antibody or a fragment thereof as claimed in claim 1 that binds the chemotactic epitope comprising the sequence SRSRY (SEQ ID NO: 10).

3. The monoclonal antibody or a fragment thereof as claimed in claim 1 that binds the chemotactic epitope comprising the sequence AVTY (SEQ ID NO: 11).

4. The monoclonal antibody or a fragment thereof as claimed in claim 1 that binds the chemotactic epitope comprising the sequence AVTYSRSRY (SEQ ID NO: 13).

5. The monoclonal antibody or a fragment thereof as claimed in claim 1 that binds the chemotactic epiptope comprising the sequence AVTYSRSRYLEC (SEQ ID NO: 9).

6. The monoclonal antibody or a fragment thereof as claimed in claim 1 that binds the chemotactic epiptope comprising the sequence YSRSRY (SEQ ID NO: 19) or SRSRYL (SEQ ID NO: 20), or both.

7. The monoclonal antibody or a fragment thereof as claimed in claim 1 that binds an epitope comprising the sequence AVTYSRSRYLEC (SEQ ID NO: 9), or a stretch of 4-12 contiguous amino acids of the sequence AVTYSRSRYLEC (SEQ ID NO: 9).

8. The monoclonal antibody or fragment thereof as claimed in claim 7 that binds an epitope comprising a stretch of at least 5 contiguous amino acids of the sequence AVTYSRSRYLEC (SEQ ID NO: 9).

9. The monoclonal antibody or fragment thereof as claimed in claim 8 that binds an epitope comprising a stretch of at least 6 contiguous amino acids of the sequence AVTYSRSRYLEC (SEQ ID NO: 9).

10. The monoclonal antibody or a fragment thereof as claimed in claim 1 that binds in vivo or in vitro generated, or both, chemotactically active uPAR fragments.

11. The monoclonal antibody or a fragment thereof according to claim 1, which is selected from a single chain antibody or a short chain antibody fragment wherein at least the complementary determination region (CDR-region) is maintained.

12. The monoclonal antibody or a fragment or an thereof according to claim 1, which is a genetically modified monoclonal antibody, and wherein at least the complementary determination region (CDR-region) is maintained.

13. The monoclonal antibody, fragment or immunological equivalent thereof according to claim 12, wherein the genetically modified monoclonal antibody is selected from the group consisting of a chimeric antibody or a partially or fully humanized antibody.

14. The monoclonal antibody or a fragment thereof as claimed in claim 1, capable of binding the uPAR fragment $D2D3_{84-274}$, $D2D3_{85-274}$, $D2D3_{86-274}$, $D2D3_{82-274}$, $D2D3_{88-274}$, $D2D3_{89-274}$ or $D2D3_{90-274}$.

15. The monoclonal antibody or a fragment thereof as claimed in claim 14, capable of binding the uPAR fragment $D2D3_{84-274}$.

16. The monoclonal antibody or a fragment thereof as claimed in claim 1, capable of binding the uPAR fragment $D2D3_{84-274}$ in a concentration of at least 0.250 ng/ml.

17. The monoclonal antibody, fragment or immunological equivalent thereof as claimed in claim 16, capable of specifically recognizing the uPAR fragment $D2D3_{84-274}$ in a concentration of at least 0.125 ng/ml.

18. The monoclonal antibody, fragment or immunological equivalent thereof as claimed in claim 16, capable of specifically recognizing the uPAR fragment $D2D3_{84-274}$ in a concentration of at least 0.0125 ng/ml.

19. The monoclonal antibody, fragment or immunological equivalent thereof as claimed in claim 16, capable of specifically recognizing the uPAR fragment $D2D3_{84-274}$ in a concentration of at least 0.00125 ng/ml.

20. The monoclonal antibody or a fragment thereof as claimed in claim 1, having a specificity for the uPAR fragment $D2D3_{84-274}$ which is at least 100 fold higher than for the uPAR fragment $D2D3_{93-274}$.

21. The monoclonal antibody or a fragment thereof as claimed in claim 1, capable of blocking tumor cell proliferation in vitro.

22. The monoclonal antibody or a fragment thereof as claimed in claim 1, capable of inhibiting tumor formation in vivo.

23. The monoclonal antibody or a fragment thereof as claimed in claim 1, capable of blocking cell migration.

24. The monoclonal antibody or a fragment thereof of claim 18, having an inhibitory activity of at least 40% on cell migration.

25. The monoclonal antibody or a fragment thereof according to claim 1, which is linked to a label.

26. The monoclonal antibody 7G1 as claimed in claim 1, wherein the monoclonal antibody is produced by cell line 7G1/87 deposited as Accession No. DSM ACC 2716.

27. The monoclonal antibody 8D3 as claimed in claim 1, wherein the monoclonal antibody is produced by cell line 8D3/18 deposited as Accession No. DSM ACC 2717.

28. A reagent kit comprising at least one monoclonal antibody or a fragment thereof, as claimed in claim 1 and further reagents suitable for diagnostic applications.

29. A cell producing a monoclonal antibody according to claim 1.

30. The cell according to claim 29 which is a eukaryotic, a mammalian, a CHO or a hybridoma cell.

31. Hybridoma cell line 7G1/87, deposited as Accession No. DSM ACC 2716.

32. A method of producing monoclonal antibody 7G1 comprising culturing the hybridoma cell line as claimed in claim 31 to produce monoclonal antibody 7G1, and then purifying the monoclonal antibody 7G1.

33. Hybridoma cell line 8D3/18, deposited as Accession No. DSM ACC 2717.

34. A method of producing monoclonal antibody 8D3 comprising culturing the hybridoma cell line as claimed in claim 33 to produce monoclonal antibody 8D3, and then purifying the monoclonal antibody 8D3.

35. A pharmaceutical or diagnostic composition comprising as active ingredient at least one monoclonal antibody or a fragment thereof as claimed in claim 1 and further pharmaceutically or diagnostically acceptable carriers and adjuvants.

* * * * *

UNITED STATES PATENT AND TRADEMARK OFFICE
CERTIFICATE OF CORRECTION

PATENT NO. : 7,951,589 B2
APPLICATION NO. : 11/814093
DATED : May 31, 2011
INVENTOR(S) : Massimo Resnati et al.

It is certified that error appears in the above-identified patent and that said Letters Patent is hereby corrected as shown below:

Column 2, line 27, delete "UPAR" and replace with uPAR

Column 9, line 59, delete "D2D3$8427_3$" and replace with D2D3$_{84\text{-}273}$

Column 10, line 19, delete "D2D3$_{94\text{-}274}$" and replace with D2D3$_{84\text{-}274}$

Column 15, line 6, delete "cytbfluorimetric" and replace with cytofluorimetric

Column 15, line 35, delete "C." and replace with C

Column 15, line 44, delete "∞C" and replace with °C

Signed and Sealed this
Thirtieth Day of August, 2011

David J. Kappos
*Director of the United States Patent and Trademark Office*

SEQUENCE LISTING

<160> NUMBER OF SEQ ID NOS: 20

<210> SEQ ID NO 1
<211> LENGTH: 353
<212> TYPE: DNA
<213> ORGANISM: Artificial Sequence
<220> FEATURE:
<223> OTHER INFORMATION: Human Hybridoma Cell Line
<220> FEATURE:
<221> NAME/KEY: 7G1_heavy_chain_seq1
<222> LOCATION: (1)..(353)

<400> SEQUENCE: 1

```
aggtgcagct gcaggagtca ggacctgagc tgaagaagcc tggagagaca gtcaagatct      60
cctgcaaggc ttctggttat accttcacag actattcaat gcactgggtg aagcaggctc     120
caggaaaggg tttaaagtgt atgggctgga taaacactga gaccactaag tcaacatatg     180
cagatgactt caagggacgg tttgccctct ctttggaaac ctctgccagc actgtctatt     240
tgcagatcag caacctcaaa aatgaggaca cggctacata tttctgtgct agagaggcct     300
catatggtga gtttgactac tggggccaag ggaccacggt caccgtctcc tca            353
```

<210> SEQ ID NO 2
<211> LENGTH: 117
<212> TYPE: PRT
<213> ORGANISM: Artificial Sequence
<220> FEATURE:
<223> OTHER INFORMATION: Human Hybridoma Cell Line
<220> FEATURE:
<221> NAME/KEY: 7G1_heavy_chain_seq2
<222> LOCATION: (1)..(117)

<400> SEQUENCE: 2

```
Val Gln Leu Gln Glu Ser Gly Pro Glu Leu Lys Lys Pro Gly Glu Thr
1               5                   10                  15

Val Lys Ile Ser Cys Lys Ala Ser Gly Tyr Thr Phe Thr Asp Tyr Ser
            20                  25                  30

Met His Trp Val Lys Gln Ala Pro Gly Lys Gly Leu Lys Cys Met Gly
        35                  40                  45

Trp Ile Asn Thr Glu Thr Thr Lys Ser Thr Tyr Ala Asp Asp Phe Lys
    50                  55                  60
```

```
Gly Arg Phe Ala Leu Ser Leu Glu Thr Ser Ala Ser Thr Val Tyr Leu
 65                  70                  75                  80

Gln Ile Ser Asn Leu Lys Asn Glu Asp Thr Ala Thr Tyr Phe Cys Ala
                 85                  90                  95

Arg Glu Ala Ser Tyr Gly Glu Phe Asp Tyr Trp Gly Gln Gly Thr Thr
            100                 105                 110

Val Thr Val Ser Ser
        115
```

```
<210> SEQ ID NO 3
<211> LENGTH: 336
<212> TYPE: DNA
<213> ORGANISM: Artificial Sequence
<220> FEATURE:
<223> OTHER INFORMATION: Human Hybridoma Cell Line
<220> FEATURE:
<221> NAME/KEY: 7G1_Light_Chain_Seq3
<222> LOCATION: (1)..(336)

<400> SEQUENCE: 3
gacattgtgc taacccagtc tccagcttcc ttagctgtat ctctggggca gagggccacc      60
atctcatgca gggccagcaa aagtgtcagt acatctggct atagttatat gcactggtac     120
caacagaaac caggacagcc acccaaactc ctcatctatc ttgcatccaa cctcgaatct     180
ggggtccctg ccaggttcag tggcagtggg tctgggacag acttcaccct cgacatccat     240
cctgtagagg aggaggatgc tgcaacctat tactgtcagc acagtaggga gcttccgtac     300
acgttcggag gggggaccaa gctggagctg aaacgg                               336
```

```
<210> SEQ ID NO 4
<211> LENGTH: 112
<212> TYPE: PRT
<213> ORGANISM: Artificial Sequence
<220> FEATURE:
<223> OTHER INFORMATION: Human Hybridoma Cell Line
<220> FEATURE:
<221> NAME/KEY: 7G1_Light_Chain_Seq4
<222> LOCATION: (1)..(112)

<400> SEQUENCE: 4

Asp Ile Val Leu Thr Gln Ser Pro Ala Ser Leu Ala Val Ser Leu Gly
 1               5                  10                  15

Gln Arg Ala Thr Ile Ser Cys Arg Ala Ser Lys Ser Val Ser Thr Ser
                 20                  25                  30

Gly Tyr Ser Tyr Met His Trp Tyr Gln Gln Lys Pro Gly Gln Pro Pro
             35                  40                  45

Lys Leu Leu Ile Tyr Leu Ala Ser Asn Leu Glu Ser Gly Val Pro Ala
 50                  55                  60

Arg Phe Ser Gly Ser Gly Ser Gly Thr Asp Phe Thr Leu Asp Ile His
 65                  70                  75                  80

Pro Val Glu Glu Glu Asp Ala Ala Thr Tyr Tyr Cys Gln His Ser Arg
                 85                  90                  95

Glu Leu Pro Tyr Thr Phe Gly Gly Gly Thr Lys Leu Glu Leu Lys Arg
            100                 105                 110
```

```
<210> SEQ ID NO 5
<211> LENGTH: 354
<212> TYPE: DNA
<213> ORGANISM: Artificial Sequence
<220> FEATURE:
<223> OTHER INFORMATION: Human Hybridoma Cell Line
<220> FEATURE:
```

```
<221> NAME/KEY: 8D3_Heavy_Chain_SEQ5
<222> LOCATION: (1)..(354)

<400> SEQUENCE: 5
cagatccagt tggtgcagtc tggacctgag ctgaagaagc ctggagagac agtcaagatc      60
tcctgcaagg cttctggtta taccttcaca gactattcaa tgcactggat gaagcaggct     120
ccaggaaggg atttaaagtg gatgggctgg ataaacactg agactggtga gacaaaatat     180
gcagctgact tcaggggacg gtttgccttc tctttggaaa cctctgccag cactgcctat     240
ttgcagatca acaacctcaa aaatgaggac acggctacat atttctgttc tagagaaact     300
gggacagggg ctatggacta ctgggggcaa gggaccacgg tcaccgtctc ctca           354

<210> SEQ ID NO 6
<211> LENGTH: 118
<212> TYPE: PRT
<213> ORGANISM: Artificial Sequence
<220> FEATURE:
<223> OTHER INFORMATION: Human Hybridoma Cell Line
<220> FEATURE:
<221> NAME/KEY: 8D3_heavy_chain_SEQ6
<222> LOCATION: (1)..(118)

<400> SEQUENCE: 6

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
            20                  25                  30

Ser Met His Trp Met Lys Gln Ala Pro Gly Arg Asp Leu Lys Trp Met
        35                  40                  45

Gly Trp Ile Asn Thr Glu Thr Gly Glu Thr Lys Tyr Ala Ala Asp Phe
    50                  55                  60

Arg Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ser Arg Glu Thr Gly Thr Gly Ala Met Asp Tyr Trp Gly Gln Gly Thr
            100                 105                 110

Thr Val Thr Val Ser Ser
        115

<210> SEQ ID NO 7
<211> LENGTH: 326
<212> TYPE: DNA
<213> ORGANISM: Artificial Sequence
<220> FEATURE:
<223> OTHER INFORMATION: Human Hybridoma Cell Line
<220> FEATURE:
<221> NAME/KEY: 8d3_light_chain_seq7
<222> LOCATION: (1)..(326)

<400> SEQUENCE: 7
gaaaatgtgc tcacccagtc tccagcaatc atgtctgcat ctctagggga acgggtcacc      60
atgacctgca ctgccagctc aagtgtaagt tccagttact tgcactggta ccagcagaag     120
ccaggatcct cccccaaact ctggatttat agcacatcca acctggcttc tggagtccca     180
gctcgcttca gtggcagtgg gtctgggacc tcttactctc tcacaatcag aagcatggag     240
gctgaagatg ctgccactta ttactgccac cagtatcatc gttccccacc cacgttcgga     300
gggggcacca agctggaaat caaacg                                         326
```

```
<210> SEQ ID NO 8
<211> LENGTH: 108
<212> TYPE: PRT
<213> ORGANISM: Artificial Sequence
<220> FEATURE:
<223> OTHER INFORMATION: Human Hybridoma Cell Line
<220> FEATURE:
<221> NAME/KEY: 8D3_light_chain_seq8
<222> LOCATION: (1)..(108)

<400> SEQUENCE: 8

Glu Asn Val Leu Thr Gln Ser Pro Ala Ile Met Ser Ala Ser Leu Gly
1               5                   10                  15

Glu Arg Val Thr Met Thr Cys Thr Ala Ser Ser Ser Val Ser Ser Ser
            20                  25                  30

Tyr Leu His Trp Tyr Gln Gln Lys Pro Gly Ser Ser Pro Lys Leu Trp
        35                  40                  45

Ile Tyr Ser Thr Ser Asn Leu Ala Ser Gly Val Pro Ala Arg Phe Ser
    50                  55                  60

Gly Ser Gly Ser Gly Thr Ser Tyr Ser Leu Thr Ile Arg Ser Met Glu
65                  70                  75                  80

Ala Glu Asp Ala Ala Thr Tyr Tyr Cys His Gln Tyr His Arg Ser Pro
                85                  90                  95

Pro Thr Phe Gly Gly Gly Thr Lys Leu Glu Ile Lys
            100                 105

<210> SEQ ID NO 9
<211> LENGTH: 12
<212> TYPE: PRT
<213> ORGANISM: Artificial
<220> FEATURE:
<223> OTHER INFORMATION: Linker Region between D1 and D2 of uPAR

<400> SEQUENCE: 9

Ala Val Thr Tyr Ser Arg Ser Arg Tyr Leu Glu Cys
1               5                   10

<210> SEQ ID NO 10
<211> LENGTH: 5
<212> TYPE: PRT
<213> ORGANISM: Artificial
<220> FEATURE:
<223> OTHER INFORMATION: Derived from linker region between D1 and D2
      of uPAR

<400> SEQUENCE: 10

Ser Arg Ser Arg Tyr
1               5

<210> SEQ ID NO 11
<211> LENGTH: 4
<212> TYPE: PRT
<213> ORGANISM: Artificial
<220> FEATURE:
<223> OTHER INFORMATION: Derived from linker region between D1 and D2
      of uPAR

<400> SEQUENCE: 11

Ala Val Thr Tyr
1

<210> SEQ ID NO 12
<211> LENGTH: 8
<212> TYPE: PRT
<213> ORGANISM: Artificial
<220> FEATURE:
```

```
<223> OTHER INFORMATION: Derived from linker region between D1 and D2
      of uPAR

<400> SEQUENCE: 12

Ser Arg Ser Arg Tyr Leu Glu Cys
1               5

<210> SEQ ID NO 13
<211> LENGTH: 9
<212> TYPE: PRT
<213> ORGANISM: Artificial
<220> FEATURE:
<223> OTHER INFORMATION: Derived from linker region between D1 and D2
      of uPAR

<400> SEQUENCE: 13

Ala Val Thr Tyr Ser Arg Ser Arg Tyr
1               5

<210> SEQ ID NO 14
<211> LENGTH: 9
<212> TYPE: PRT
<213> ORGANISM: Artificial
<220> FEATURE:
<223> OTHER INFORMATION: Derived from linker region between D1 and D2
      of uPAR

<400> SEQUENCE: 14

Tyr Ser Arg Ser Arg Tyr Leu Glu Cys
1               5

<210> SEQ ID NO 15
<211> LENGTH: 6
<212> TYPE: PRT
<213> ORGANISM: Artificial
<220> FEATURE:
<223> OTHER INFORMATION: Derived from linker region between D1 and D2
      of uPAR

<400> SEQUENCE: 15

Ser Arg Tyr Leu Glu Cys
1               5

<210> SEQ ID NO 16
<211> LENGTH: 14
<212> TYPE: PRT
<213> ORGANISM: Artificial
<220> FEATURE:
<223> OTHER INFORMATION: Tagging sequence for C-terminus of mutant
      receptors

<400> SEQUENCE: 16

His Arg Arg Ala Ser Val Asp Tyr Lys Asp Asp Asp Asp Lys
1               5                   10

<210> SEQ ID NO 17
<211> LENGTH: 4
<212> TYPE: PRT
<213> ORGANISM: Artificial
<220> FEATURE:
<223> OTHER INFORMATION: Derived from linker region between D1 and D2
      of uPAR

<400> SEQUENCE: 17

Tyr Leu Glu Cys
1

<210> SEQ ID NO 18
```

```
<211> LENGTH: 3
<212> TYPE: PRT
<213> ORGANISM: Artificial
<220> FEATURE:
<223> OTHER INFORMATION: Derived from linker region between D1 and D2
      of uPAR

<400> SEQUENCE: 18

Leu Glu Cys
1

<210> SEQ ID NO 19
<211> LENGTH: 6
<212> TYPE: PRT
<213> ORGANISM: Artificial
<220> FEATURE:
<223> OTHER INFORMATION: Derived from linker region between D1 and D2
      of uPAR

<400> SEQUENCE: 19

Tyr Ser Arg Ser Arg Tyr
1               5

<210> SEQ ID NO 20
<211> LENGTH: 6
<212> TYPE: PRT
<213> ORGANISM: Artificial
<220> FEATURE:
<223> OTHER INFORMATION: Derived from linker region between D1 and D2
      of uPAR

<400> SEQUENCE: 20

Ser Arg Ser Arg Tyr Leu
1               5
```